(12) United States Patent
Kikuchi et al.

(10) Patent No.: US 10,729,307 B2
(45) Date of Patent: Aug. 4, 2020

(54) IMAGE PROCESSING DEVICE, IMAGE PROCESSING METHOD, AND SURGICAL SYSTEM

(71) Applicant: SONY CORPORATION, Tokyo (JP)

(72) Inventors: Daisuke Kikuchi, Kanagawa (JP); Takami Mizukura, Kanagawa (JP); Tsuneo Hayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 311 days.

(21) Appl. No.: 15/568,887

(22) PCT Filed: May 25, 2016

(86) PCT No.: PCT/JP2016/065387
§ 371 (c)(1),
(2) Date: Oct. 24, 2017

(87) PCT Pub. No.: WO2016/194718
PCT Pub. Date: Dec. 8, 2016

(65) Prior Publication Data
US 2018/0098683 A1     Apr. 12, 2018

(30) Foreign Application Priority Data
Jun. 5, 2015 (JP) .................................. 2015-114912

(51) Int. Cl.
*A61B 1/00* (2006.01)
*A61B 5/00* (2006.01)
(Continued)

(52) U.S. Cl.
CPC ............ *A61B 1/00009* (2013.01); *A61B 1/04* (2013.01); *A61B 1/3132* (2013.01); *A61B 5/024* (2013.01);
(Continued)

(58) Field of Classification Search
None
See application file for complete search history.

(56) References Cited

U.S. PATENT DOCUMENTS

2008/0243162 A1* 10/2008 Shibata ............. A61B 17/3417
                                                                                      606/185
2010/0081875 A1*  4/2010 Fowler ............... A61B 1/00149
                                                                                       600/114
(Continued)

FOREIGN PATENT DOCUMENTS

| JP | 2007-61638 A | 3/2007 |
| JP | 2011-24628 A | 2/2011 |
| JP | 2014-3990 A | 1/2014 |

OTHER PUBLICATIONS

JP2014075999 english translation "Motion Detection Method for Cardiac Muscle Cells, Image Processing Program and Image Processing Apparatus, Culture Method for Cardiac Muscle Cells, and Drug Evaluation Method and Drug Manufacturing Method for Cardiac Muscle Cells" Masabumi et al Oct. 10, 2012 (Year: 2012).*

*Primary Examiner* — Nancy Bitar
(74) *Attorney, Agent, or Firm* — Xsensus LLP

(57) ABSTRACT

The present disclosure relates to an image processing device, an image processing method, and a surgical system that enable detection of a region including a specific living body site in an intraoperative image on the basis of a frequency of a motion vector of a living body in the intraoperative image. A motion detection unit detects the motion vector of the living body in the intraoperative image using the intraoperative images at different times. The analysis unit obtains the frequency of the motion vector detected by the motion detection unit. A frequency map generation unit detects the region including the specific living body site in the intraoperative image on the basis of the frequency obtained by the analysis unit. The present disclosure is applicable to, for (Continued)

example, a CCU and the like of an endoscopic surgical system.

17 Claims, 20 Drawing Sheets

(51) Int. Cl.
| | |
|---|---|
| *G06T 7/215* | (2017.01) |
| *A61B 90/00* | (2016.01) |
| *A61B 18/14* | (2006.01) |
| *A61B 1/04* | (2006.01) |
| *A61B 90/20* | (2016.01) |
| *A61B 1/313* | (2006.01) |
| *A61B 5/02* | (2006.01) |
| *A61B 5/024* | (2006.01) |
| *A61B 5/11* | (2006.01) |
| *A61B 17/34* | (2006.01) |
| *A61B 17/00* | (2006.01) |
| *A61B 34/20* | (2016.01) |

(52) U.S. Cl.
CPC ...... *A61B 5/02007* (2013.01); *A61B 5/02042* (2013.01); *A61B 5/1128* (2013.01); *A61B 5/489* (2013.01); *A61B 5/7289* (2013.01); *A61B 17/3423* (2013.01); *A61B 17/3474* (2013.01); *A61B 18/14* (2013.01); *A61B 90/20* (2016.02); *A61B 90/361* (2016.02); *A61B 90/37* (2016.02); *G06T 7/215* (2017.01); *A61B 2017/00119* (2013.01); *A61B 2017/00699* (2013.01); *A61B 2017/00703* (2013.01); *A61B 2017/00973* (2013.01); *A61B 2034/2065* (2016.02); *A61B 2090/364* (2016.02); *A61B 2090/373* (2016.02); *G06T 2207/30048* (2013.01)

(56) References Cited

U.S. PATENT DOCUMENTS

| | | | |
|---|---|---|---|
| 2014/0226069 A1* | 8/2014 | Oshima | G06T 7/20 348/584 |
| 2014/0303491 A1* | 10/2014 | Shekhar | A61B 8/5261 600/424 |
| 2015/0282695 A1* | 10/2015 | Tay | A61B 1/00135 600/124 |
| 2017/0231553 A1* | 8/2017 | Igarashi | A61B 5/0285 600/479 |

* cited by examiner

IMAGE PROCESSING DEVICE, IMAGE PROCESSING METHOD, AND SURGICAL SYSTEM

TECHNICAL FIELD

The present disclosure relates to an image processing device, an image processing method, and a surgical system, and especially relates to an image processing device, an image processing method, and a surgical system that enable detection of a region including a specific living body site in an intraoperative image on the basis of a frequency of a motion vector of a living body in the intraoperative image.

BACKGROUND ART

There is an image processing device that detects a feature amount such as color information and edge information from an intraoperative image captured by an endoscope and detects a region of a blood vessel in the intraoperative image on the basis of the feature amount (refer to Patent Document 1, for example).

CITATION LIST

Patent Document

Patent Document 1: Japanese Patent Application Laid-Open No. 2007-61638

SUMMARY OF THE INVENTION

Problems to be Solved by the Invention

However, it is difficult to detect with a high degree of accuracy a region of a specific living body site in an intraoperative image on the basis of a feature amount of the intraoperative image. For example, it is sometimes impossible to discriminate a region of a blood vessel from a region of a neural tube and the like other than the blood vessel.

The present disclosure is achieved in view of such a situation, and an object thereof is to enable detection of a region including a specific living body site in the intraoperative image on the basis of a frequency of a motion vector of a living body in the intraoperative image.

Solutions to Problems

An image processing device according to a first aspect of the present disclosure is an image processing device provided with a motion detection unit that detects a motion vector of a living body in an intraoperative image using intraoperative images at different times, an analysis unit that obtains a frequency of the motion vector detected by the motion detection unit, and a region detection unit that detects a region including a specific living body site in the intraoperative image on the basis of the frequency obtained by the analysis unit.

An image processing method according to the first aspect of the present disclosure corresponds to the image processing device according to the first aspect of the present disclosure.

In the first aspect of the present disclosure, the motion vector of the living body in the intraoperative image is detected using the intraoperative images at different times, the frequency of the motion vector is obtained, and the region including the specific living body site in the intraoperative image is detected on the basis of the frequency.

Meanwhile, the image processing device according to the first aspect may be realized by allowing a computer to execute a program.

Also, in order to realize the image processing device according to the first aspect, the program to be executed by the computer may be provided by being transmitted via a transmission medium or by being recorded on a recording medium.

A surgical system according to a second aspect of the present disclosure is a surgical system provided with an imaging device that captures an intraoperative image, and an image processing device that performs image processing on the intraoperative image, in which the image processing device is provided with a motion detection unit that detects a motion vector of a living body in the intraoperative image using intraoperative images at different times, an analysis unit that obtains a frequency of the motion vector detected by the motion detection unit, and a region detection unit that detects a region including a specific living body site in the intraoperative image on the basis of the frequency obtained by the analysis unit.

In the second aspect of the present disclosure, the intraoperative image is captured and the image processing is performed on the intraoperative image. The image processing includes detecting the motion vector of the living body in the intraoperative image using the intraoperative images at different times, obtaining the frequency of the detected motion vector, and detecting the region including the specific living body site in the intraoperative image on the basis of the frequency.

Effects of the Invention

According to the first and second aspects of the present disclosure, it is possible to perform image processing on an intraoperative image. Also, according to the first and second aspects of the present disclosure, it is possible to detect a region including a specific living body site in the intraoperative image on the basis of a frequency of a motion vector of a living body in the intraoperative image.

Meanwhile, the effects are not necessarily limited to the effects herein described and may include any of the effects described in the present disclosure.

MODE FOR CARRYING OUT THE INVENTION

A mode for carrying out the present disclosure (hereinafter, referred to as an embodiment) is hereinafter described. Meanwhile, the description is given in the following order.

1. First Embodiment: Endoscopic Surgical System (FIGS. 1 to 5)
2. Second Embodiment: Endoscopic Surgical System (FIGS. 6 to 8)
3. Third Embodiment: Endoscopic Surgical System (FIGS. 9 to 12)
4. Fourth Embodiment: Endoscopic Surgical System (FIGS. 13 to 16)
5. Fifth Embodiment: Endoscopic Surgical System (FIGS. 17 to 19)
6. Sixth Embodiment: Endoscopic Surgical System (FIGS. 20 to 22)
7. Seventh Embodiment: Computer (FIG. 23)

First Embodiment (Configuration Example of First Embodiment of Endoscopic Surgical System)

Figure 1:
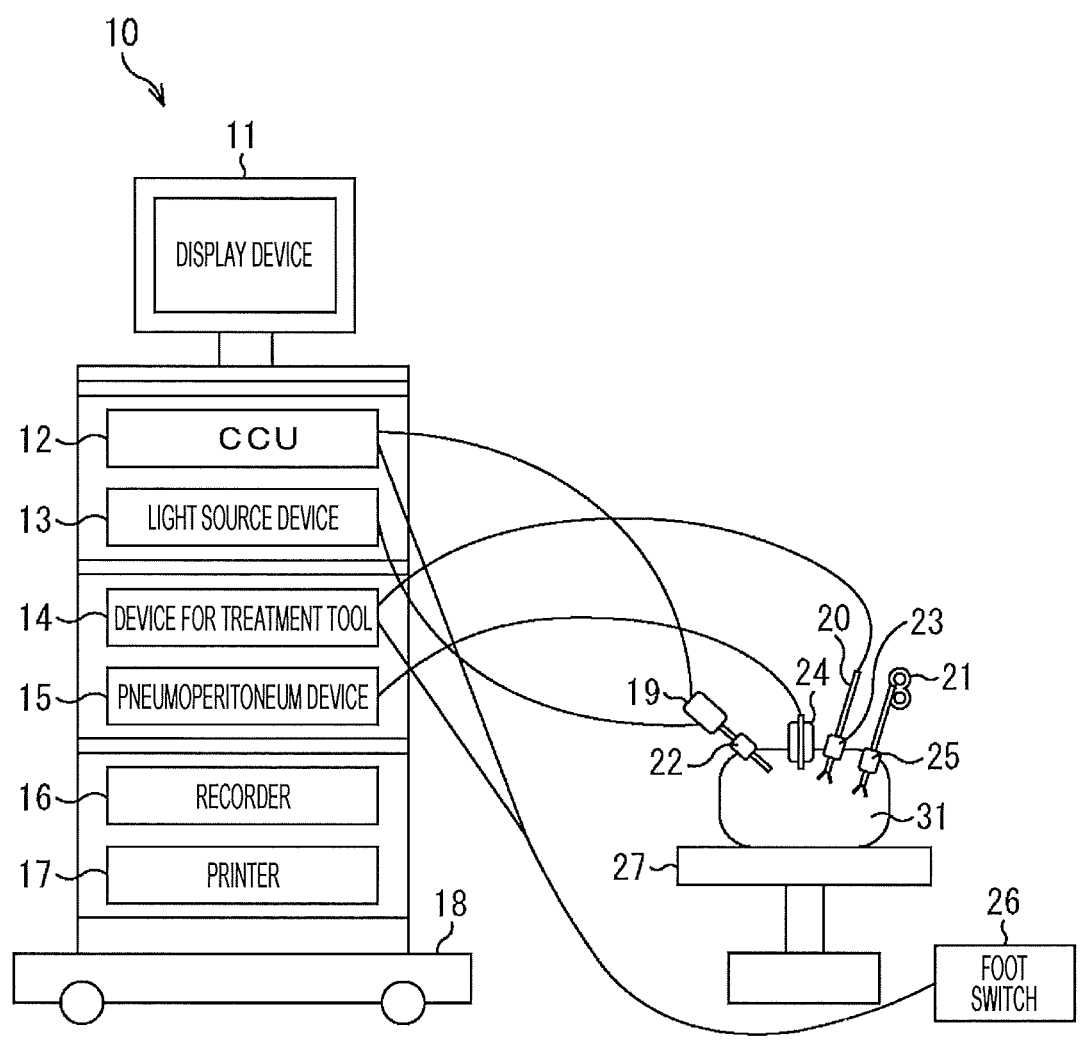
FIG. 1 is a view illustrating a configuration example according to a first embodiment of an endoscopic surgical system to which the present disclosure is applied.

FIG. 1 is a view illustrating a configuration example of a first embodiment of an endoscopic surgical system to which the present disclosure is applied.

An endoscopic surgical system 10 is provided with a cart 18 on which a display device 11, a camera control unit (CCU) 12, a light source device 13, a device for treatment tool 14, a pneumoperitoneum device 15, a recorder 16, and a printer 17 are mounted. The endoscopic surgical system 10 also includes an endoscope (laparoscope) 19, an energy treatment tool 20, forceps 21, trocars 22 to 25, a foot switch 26, and a patient bed 27. The endoscopic surgical system 10 arranged in, for example, an operating room supports a surgeon performing laparoscopic surgery on an affected site included in the abdomen 31 of a patient lying on the patient bed 27.

Specifically, the display device 11 of the endoscopic surgical system 10 is formed of a stationary 2D display, a head-mounted display and the like. The display device 11 displays an intraoperative image and the like supplied from the CCU 12.

The CCU 12 is connected to the endoscope 19 via a camera cable. Meanwhile, the CCU 12 may also be wirelessly connected to the endoscope 19. The CCU 12 receives the intraoperative image in frame unit captured by the endoscope 19 and transmitted via the camera cable. The CCU 12 supplies the received intraoperative image to the recorder 16 and the printer 17 as needed.

Also, the CCU 12 (image processing device) performs image processing on the intraoperative image. In response to an operation signal supplied from the foot switch 26, the CCU 12 switches between the intraoperative image and an image processing result and supplies the same to the display device 11 to display.

The light source device 13 is connected to the endoscope 19 via a light guide cable. The light source device 13 switches light of various wavelengths (white light, special light and the like) and emits the same to the endoscope 19.

The device for treatment tool 14 being a high-frequency output device is connected to the energy treatment tool 20 and the foot switch 26 via cables. The device for treatment tool 14 outputs high-frequency current to the energy treatment tool 20 in response to the operation signal supplied from the foot switch 26.

The pneumoperitoneum device 15 provided with air supply means and air suction means supplies air in the abdomen 31 through a hole of the trocar 24 being a hole making tool attached to an abdominal wall of the abdomen 31.

The recorder 16 records the intraoperative image supplied from the CCU 12. The printer 17 prints the intraoperative image supplied from the CCU.

The endoscope 19 (imaging device) is formed of a scope provided with an imaging unit and an optical system such as an illumination lens, a camera head and the like. The endoscope 19 is inserted into the abdomen 31 to be operated through a hole of the trocar 22 attached to the abdominal wall of the abdomen 31. The optical system of the endoscope 19 irradiates the inside of the abdomen 31 with the light emitted from the light source device 13 and supplied through the camera head, and the imaging unit captures the intraoperative image in the abdomen 31. The endoscope 19 supplies the intraoperative image to the CCU 12 via the camera head and the camera cable.

The energy treatment tool 20 is formed of an electric scalpel and the like. The energy treatment tool 20 is inserted into the abdomen 31 through a hole of the trocar 23 attached to the abdominal wall of the abdomen 31. The energy treatment tool 20 denatures or cuts the inside of the abdomen 31 using electric heat.

The forceps 21 are inserted into the abdomen 31 through a hole of the trocar 25 attached to the abdominal wall of the abdomen 31. The forceps 21 grasp the inside of the abdomen 31. The endoscope 19, the energy treatment tool 20, and the forceps 21 are grasped by the surgeon, an assistant, a scopist, a robot and the like.

The foot switch 26 accepts an operation by a foot of the surgeon, the assistant and the like. The foot switch 26 supplies the operation signal indicating the accepted operation to the CCU 12 and the device for treatment tool 14.

In the endoscopic surgical system 10 configured in the above-described manner, the surgeon and the like switches a display target of the display device 11 from one of the intraoperative image and the image processing result to the other by operating the foot switch 26.

(Configuration Example of CCU)

Figure 2:
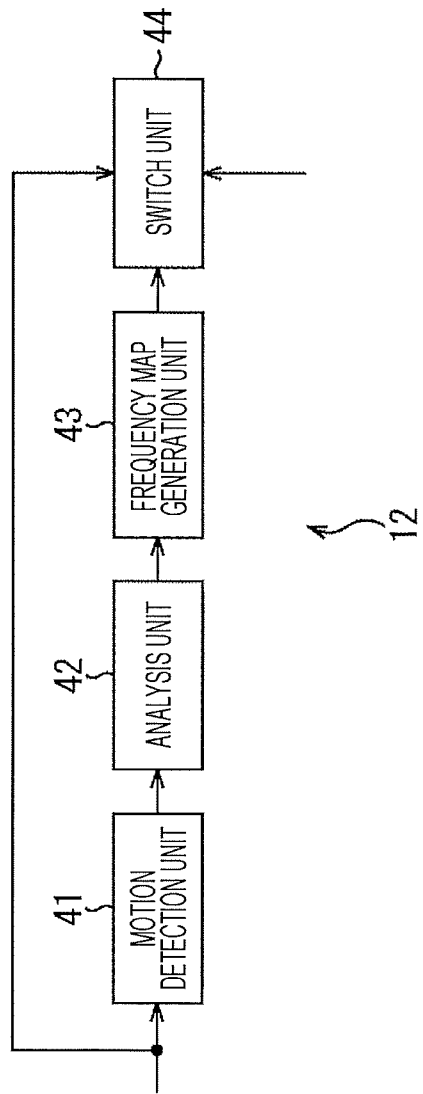
FIG. 2 is a block diagram illustrating a configuration example of a CCU in FIG. 1.

FIG. 2 is a block diagram illustrating a configuration example of the CCU 12 in FIG. 1.

The CCU 12 in FIG. 2 is formed of a motion detection unit 41, an analysis unit 42, a frequency map generation unit 43, and a switch unit 44.

The motion detection unit 41 of the CCU 12 receives the intraoperative image in frame unit from the endoscope 19 in FIG. 1 to hold. The motion detection unit 41 also uses the intraoperative image and the held intraoperative image of a frame (time) prior to the intraoperative image to detect a motion vector indicating a motion amount and a motion direction of a living body in the intraoperative image for each detection unit (for example, one or more pixels). As a method of detecting the motion vector, there are a block matching method, a gradient method and the like. The motion detection unit 41 supplies the motion vector of each detection unit of the intraoperative image to the analysis unit 42.

The analysis unit 42 holds the motion vectors as many as analysis frames being a plurality of frames (for example, 60 frames (one second)) supplied from the motion detection unit 41. The analysis unit 42 resolves the held motion vectors as many as the analysis frames into the motion vectors in a horizontal direction and a vertical direction. The analysis unit 42 obtains a frequency of the motion vector with a larger maximum value of the motion amount out of the motion vectors in the horizontal direction and in the vertical direction as many as the analysis frames for each detection unit.

As a method of obtaining the frequency of the motion vector, there is a method of performing fast Fourier transform (FFT) on the motion vector, for example. As a result, in the detection unit in which a predetermined change in time of the motion vector is repeated in the analysis frames, the frequency corresponding to a period of the change in time is obtained. As the number of frames forming the analysis frames is larger, accuracy of the frequency is improved, but since it requires much calculation time, a real-time property is lost. The analysis unit 42 supplies a frequency image representing the frequency of each pixel as a pixel value to the frequency map generation unit 43.

On the basis of the frequency image supplied from the analysis unit 42, the frequency map generation unit 43 detects a region in the image formed of successive detection units whose frequencies are close to each other and generates a frequency map representing a position in the image of the region and an average value of the frequencies.

Specifically, the frequency map generation unit 43 (region detection unit) smooths the frequency image, performs region division for each frequency on the smoothed frequency image, and detects a region including a specific living body site (for example, a specific organ, a blood vessel, blood and the like) corresponding to each frequency. Meanwhile, the detection unit the frequency of which cannot be obtained is divided as a frequency indefinite region. The frequency map generation unit 43 generates the frequency map representing each region in the frequency image in a color assigned to the frequency corresponding to the region to supply to the switch unit 44.

In response to the operation signal transmitted from the foot switch 26, the switch unit 44 selects the intraoperative image in frame unit transmitted from the endoscope 19 or the frequency map supplied from the frequency map generation unit 43. The switch unit 44 transmits the selected intraoperative image or frequency map to the display device 11 in FIG. 1.

(Description of Frequency of Motion Vector in Horizontal Direction)

Figure 3:
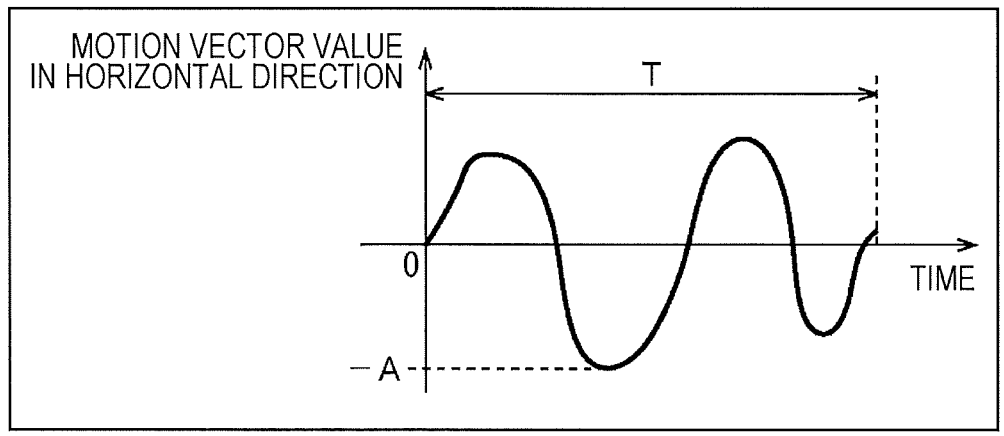
FIG. 3 is a view illustrating a frequency of a motion vector in a horizontal direction.

FIG. 3 is a view illustrating the frequency of the motion vector in the horizontal direction obtained by the analysis unit 42.

In FIG. 3, the abscissa axis represents time (frame) and the ordinate axis represents a motion vector value in the horizontal direction. The motion vector value is a value representing a direction of motion represented by the motion vector as a positive or negative value and represents the motion amount as a value. In a case where the direction of the motion represented by the motion vector is a direction to the right, for example, the motion vector value in the horizontal direction is a positive value, and in a case of a direction to the left, the motion vector value is a negative value.

In an example in FIG. 3, an absolute value (amplitude) of the motion vector value in the horizontal direction during time T corresponding to the number of analysis frames, that is, the maximum value of the motion amount is an absolute value A. In a case where the absolute value A is larger than the maximum value of the absolute value of the motion vector value in the vertical direction, the analysis unit 42 detects the frequency of the motion vector in the horizontal direction. In the example in FIG. 3, since a predetermined change in time of the motion vector value in the horizontal direction is repeated twice, the frequency corresponding to a period ½ T is detected as the frequency of the motion vector in the horizontal direction.

Meanwhile, although not illustrated, the frequency of the motion vector in the vertical direction may also be obtained in the manner similar to that of the frequency of the motion vector in the horizontal direction.

(Example of Frequency Map)

Figure 4:
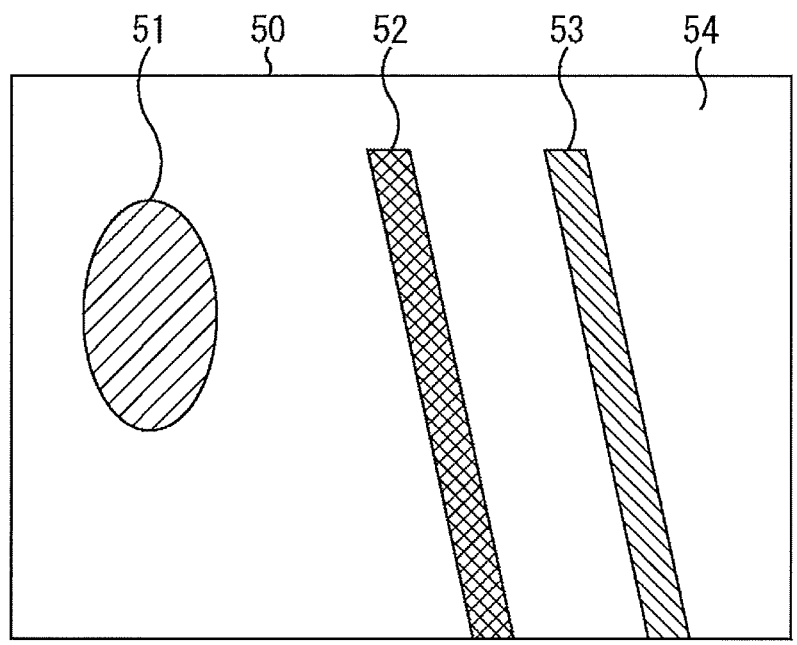
FIG. 4 is a view illustrating an example of a frequency map.

FIG. 4 is a view illustrating an example of the frequency map.

In the example in FIG. 4, the smoothed frequency image is formed of the detection units indicating 1 Hz, 40 Hz, or 2 Hz and the detection unit the frequency of which cannot be obtained. In this case, the frequency map generation unit 43 divides the smoothed frequency image into a total of four regions which are regions 51 to 53 in which the frequencies are 1 Hz, 40 Hz, and 2 Hz, respectively, and a frequency indefinite region 54 the frequency of which cannot be obtained.

Then, the frequency map generation unit 43 assigns different colors to the regions 51 to 53 and the frequency indefinite region 54 and generates a frequency map 50 in which the colors of the regions 51 to 53 and the frequency indefinite region 54 are different from one another.

(Description of Processing of CCU)

Figure 5:
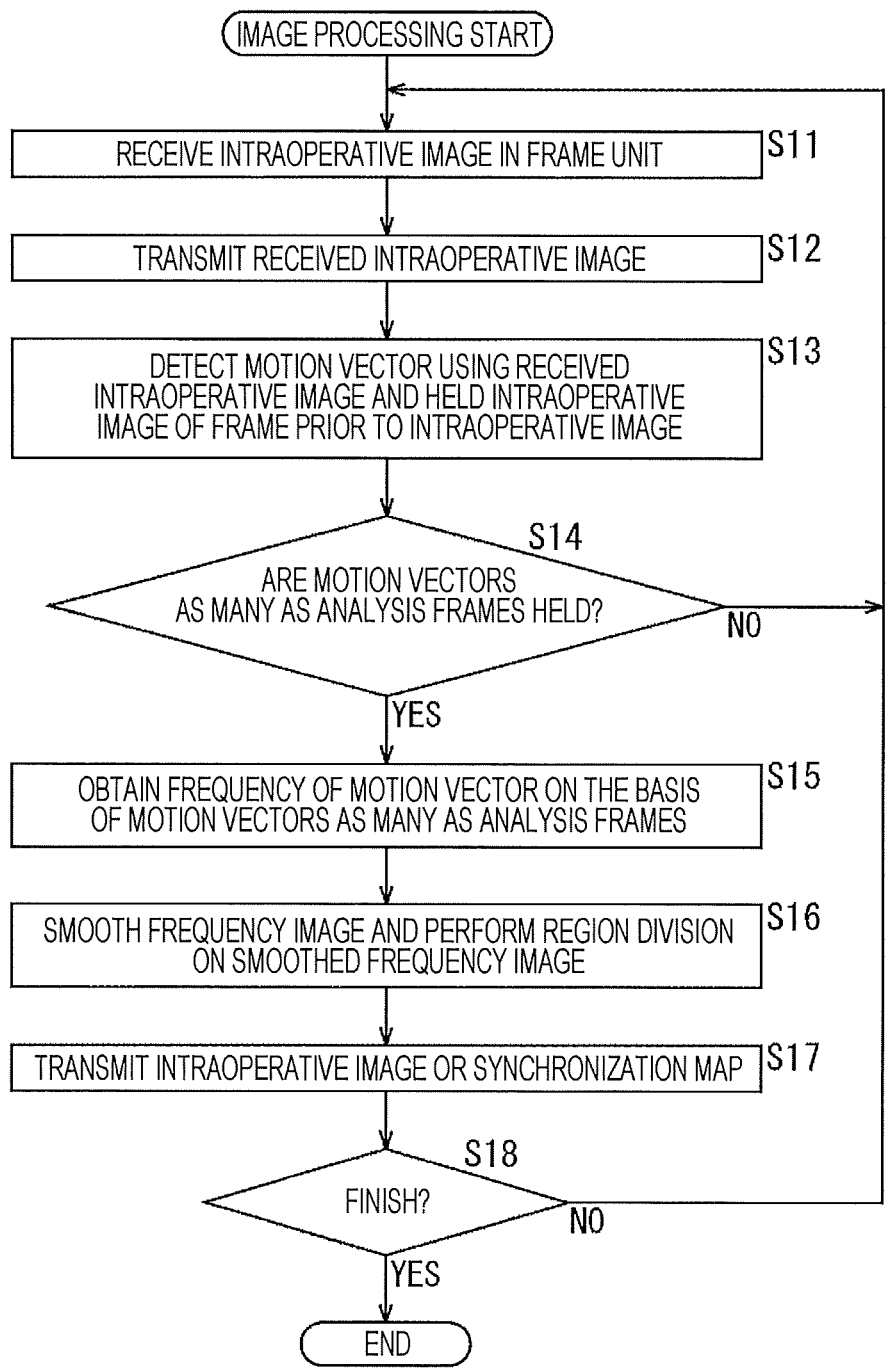
FIG. 5 is a flowchart illustrating image processing of the CCU in FIG. 2.

FIG. 5 is a flowchart illustrating image processing of the CCU 12 in FIG. 2.

At step S11 in FIG. 5, the motion detection unit 41 and the switch unit 44 of the CCU 12 receive the intraoperative image in frame unit from the endoscope 19 in FIG. 1. The motion detection unit 41 holds the received intraoperative image in frame unit.

At step S12, the switch unit 44 transmits the received intraoperative image in frame unit to the display device 11 in FIG. 1.

At step S13, the motion detection unit 41 uses the intraoperative image in frame unit received at step S11 and the held intraoperative image of the frame prior to the intraoperative image to detect the motion vector of the living body in the intraoperative image for each detection unit. The motion detection unit 41 supplies the motion vector of each detection unit of the intraoperative image to the analysis unit 42. The analysis unit 42 holds the motion vector supplied from the motion detection unit 41.

At step S14, the analysis unit 42 determines whether the motion vectors as many as the analysis frames are held. In a case where it is determined at step S14 that the motion vectors as many as the analysis frames are not held yet, the procedure returns to step S11, and the processes at steps S11 to S14 are repeated until the analysis unit 42 holds the motion vectors as many as the analysis frames.

On the other hand, in a case where it is determined at step S14 that the motion vectors as many as the analysis frames are held, the procedure shifts to step S15. At step S15, the analysis unit 42 obtains the frequency of the motion vector for each detection unit on the basis of the held motion vectors as many as the analysis frames. The analysis unit 42 supplies the frequency image representing the obtained frequency of each pixel as the pixel value to the frequency map generation unit 43.

At step S16, the frequency map generation unit 43 smooths the frequency image supplied from the analysis unit 42 and performs the region division on the smoothed frequency image. The frequency map generation unit 43 generates the frequency map representing each divided region in a peripheral image in the color assigned to the frequency corresponding to the region. The frequency map generation unit 43 supplies the frequency map to the switch unit 44.

At step S17, the switch unit 44 transmits the intraoperative image received by the process at immediately preceding step S11 or the frequency map supplied from the frequency map generation unit 43 to the display device 11 in response to the operation signal received from the foot switch 26.

At step S18, the CCU 12 determines whether to finish the image processing, for example, whether the foot switch 26 is operated by the user for giving an instruction to finish the image processing. In a case where it is determined at step S18 that the image processing is not finished, the procedure returns to step S11, and the processes at steps S11 to S18 are performed until it is determined that the image processing is finished. At that time, in the process at step S13, the analysis unit 42 holds the motion vector supplied from the motion detection unit 41 in place of the oldest held motion vector. That is, the analysis unit 42 holds only the motion vectors corresponding to the latest analysis frames.

On the other hand, in a case where it is determined at step S18 that the image processing is finished, the procedure is finished.

As described above, the CCU 12 may detect the region including the specific living body site with the different frequency of the motion vector in the intraoperative image on the basis of the frequency of the motion vector of the living body in the intraoperative image with a high degree of accuracy. Also, since the CCU 12 switches between the frequency map and the intraoperative image to display, the surgeon and the like may easily discriminate the region of the living body site moving in synchronization with a heartbeat such as the blood vessel and a heart in the intraoperative image and the region of the living body site moving in conjunction with breathing such as lungs, and a diaphragm. As a result, improvement in accuracy and reduction in time of the surgery may be expected.

Second Embodiment (Configuration Example of CCU of Second Embodiment of Endoscopic Surgical System)

A configuration of a second embodiment of an endoscopic surgical system to which the present disclosure is applied is the same as a configuration of an endoscopic surgical system 10 in FIG. 1 except for a configuration of a CCU. Therefore, only the CCU is hereinafter described.

Figure 6:
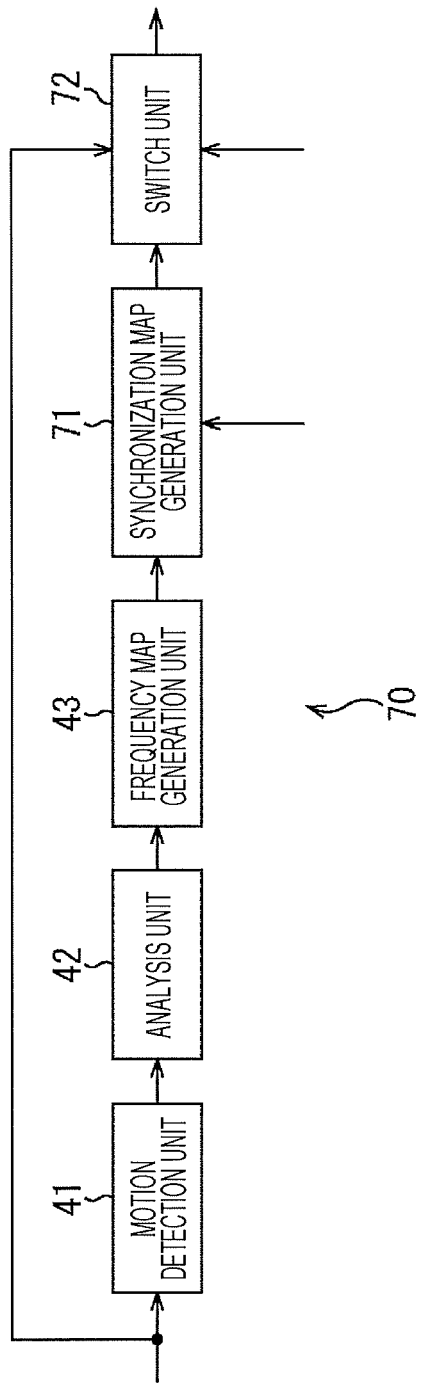
FIG. 6 is a block diagram illustrating a configuration example of a CCU according to a second embodiment of an endoscopic surgical system to which the present disclosure is applied.

FIG. 6 is a block diagram illustrating a configuration example of the CCU of the second embodiment of the endoscopic surgical system to which the present disclosure is applied.

In the configuration illustrated in FIG. 6, the same reference sign is assigned to the same configuration as that in FIG. 2. Overlapping description is appropriately omitted.

A configuration of a CCU 70 in FIG. 6 is different from a configuration of a CCU 12 in FIG. 2 in that a synchronization map generation unit 71 is newly provided and a switch unit 72 is provided in place of a switch unit 44. The CCU 70 allows a display device 11 to display not a frequency map but a synchronization map representing a region corresponding to a predetermined frequency among regions in the frequency map in a different color from that of other regions as an image processing result.

Specifically, the synchronization map generation unit 71 (region detection unit) detects a region including a specific living body site corresponding to a frequency indicated by frequency information out of the regions in the frequency map on the basis of the frequency map supplied from a frequency map generation unit 43 and the frequency information indicating the frequency input from an external device not illustrated.

In more detail, the synchronization map generation unit 71 determines whether the frequency corresponding to the region synchronizes with the frequency indicated by the frequency information for each region in a peripheral map. Then, the synchronization map generation unit 71 generates the synchronization map by deleting the region determined not to synchronize in the frequency map. Meanwhile, as the frequency information, for example, there is heartbeat information indicating a frequency determined on the basis of a heartbeat input from an electrocardiograph and the like. The synchronization map generation unit 71 supplies the synchronization map to the switch unit 72.

In response to an operation signal transmitted from a foot switch 26, the switch unit 72 transmits an intraoperative image in frame unit received from an endoscope 19 or the synchronization map supplied from the synchronization map generation unit 71 to the display device 11 in FIG. 1.

(Example of Synchronization Map)

Figure 7:
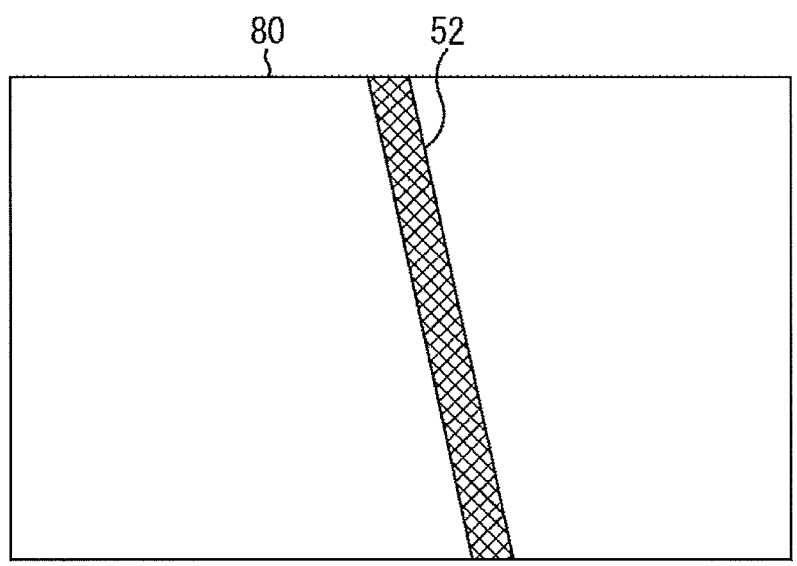
FIG. 7 is a view illustrating an example of a synchronization map.

FIG. 7 is a view illustrating an example of the synchronization map.

In the example in FIG. 7, the frequency map generation unit 43 generates a frequency map 50 in FIG. 4. Also, the frequency indicated by the frequency information is 40 Hz.

In this case, the synchronization map generation unit 71 deletes all but a region 52 corresponding to 40 Hz out of regions 51 to 53 and a frequency indefinite region 54 of the frequency map 50 to generate a synchronization map 80 in FIG. 7.

(Description of Processing of CCU)

Figure 8:
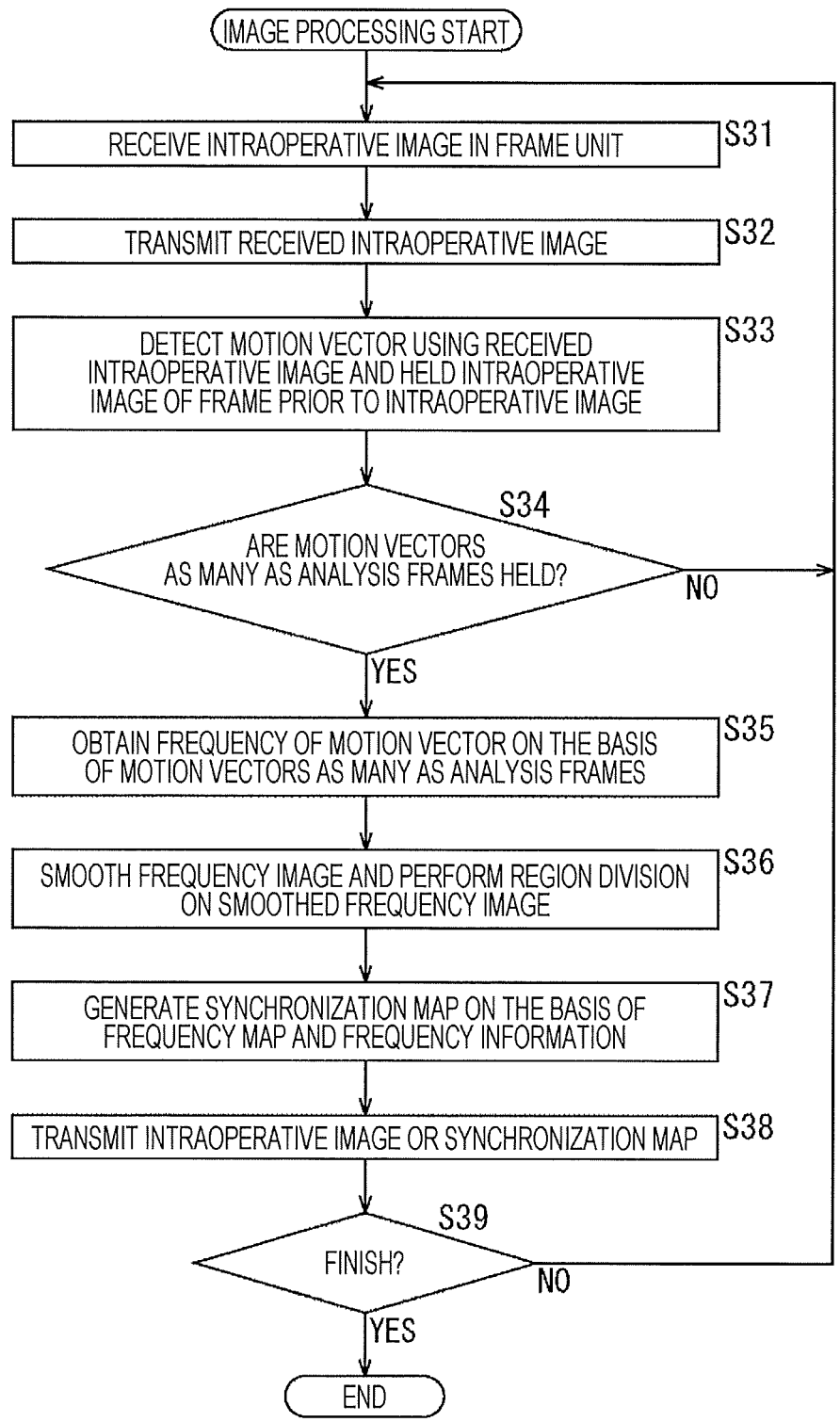
FIG. 8 is a flowchart illustrating image processing of a CCU in FIG. 6.

FIG. 8 is a flowchart illustrating image processing of the CCU 70 in FIG. 6.

Processes at steps S31 to S36 in FIG. 8 are similar to processes at steps S11 to S16 in FIG. 5, respectively, so that description thereof is omitted.

At step S37, the synchronization map generation unit 71 generates the synchronization map on the basis of the frequency map supplied from the frequency map generation unit 43 and the frequency information input from the external device not illustrated. The synchronization map generation unit 71 supplies the synchronization map to the switch unit 72.

At step S38, the switch unit 72 transmits the intraoperative image in frame unit received by the process at immediately preceding step S31 or the synchronization map supplied from the synchronization map generation unit 71 to the display device 11 in response to the operation signal received from the foot switch 26.

A process at step S39 is similar to a process at step S18 in FIG. 5, so that description thereof is omitted.

In the above-described manner, since the CCU 100 switches between the synchronization map and the intraoperative image to display, a surgeon and the like may easily discriminate a living body site moving at a predetermined frequency in the intraoperative image (for example, a blood vessel moving in synchronization with the heartbeat).

Third Embodiment (Configuration Example of CCU of Third Embodiment of Endoscopic Surgical System)

A configuration of a third embodiment of an endoscopic surgical system to which the present disclosure is applied is the same as that of an endoscopic surgical system 10 in FIG. 1 except for a configuration of a CCU. Therefore, only the CCU is hereinafter described.

Figure 9:
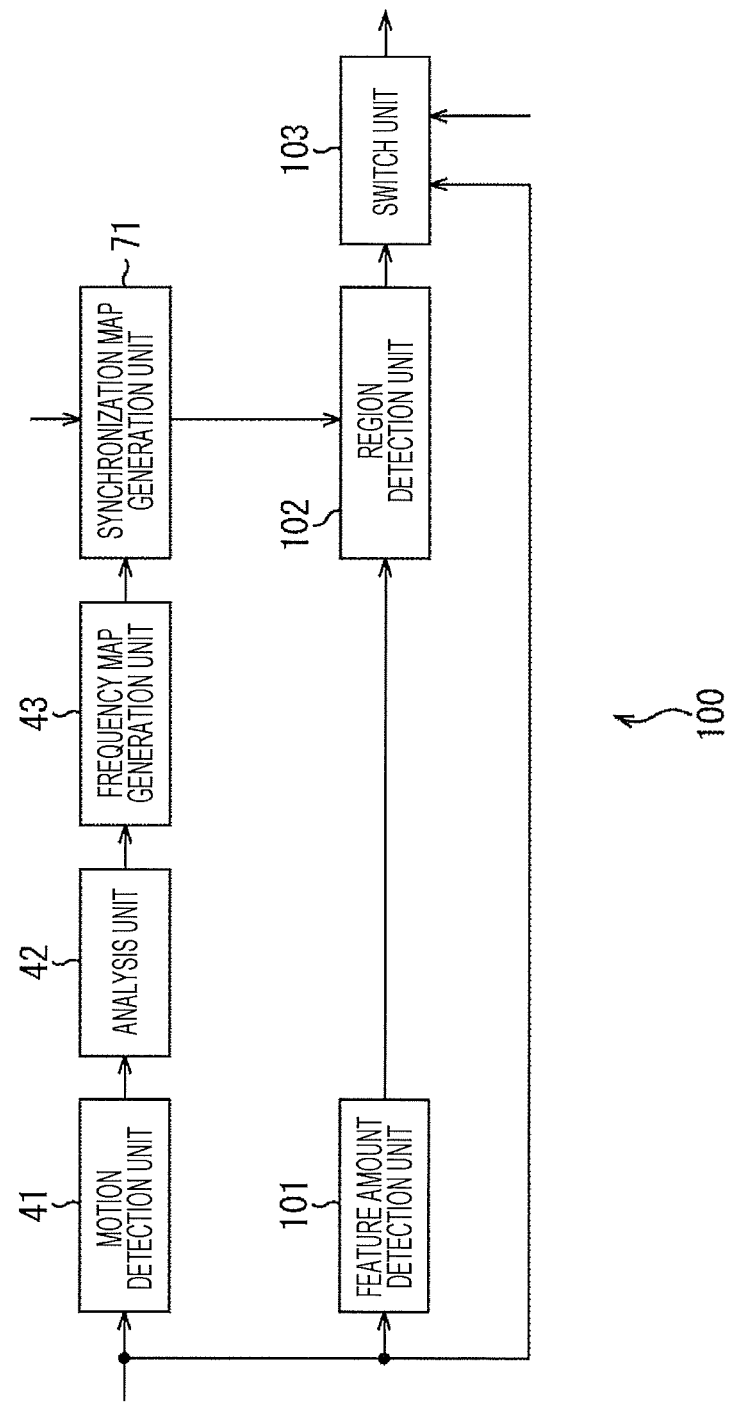
FIG. 9 is a block diagram illustrating a configuration example of a CCU according to a third embodiment of an endoscopic surgical system to which the present disclosure is applied.

FIG. 9 is a block diagram illustrating a configuration example of the CCU of the third embodiment of the endoscopic surgical system to which the present disclosure is applied.

In the configuration illustrated in FIG. 9, the same reference sign is assigned to the same configuration as that in FIG. 6. Overlapping description is appropriately omitted.

A configuration of a CCU 100 in FIG. 9 is different from a configuration of a CCU 70 in FIG. 6 in that a feature amount detection unit 101 and a region detection unit 102 are newly provided, and a switch unit 103 is provided in place of a switch unit 72. The CCU 100 detects a region of a specific organ or a blood vessel on the basis of a synchronization map and a feature amount of an intraoperative image.

Specifically, the feature amount detection unit 101 detects edge information and color information such as luminance, saturation, and hue as the feature amounts from the intraoperative image received from an endoscope 19 and supplies the same to the region detection unit 102.

The region detection unit 102 detects the region of the specific organ or the blood vessel on the basis of the synchronization map generated by a synchronization map generation unit 71 and the feature amount supplied from the feature amount detection unit 101. The region detection unit 102 supplies an organ map having the same size as the intraoperative image representing the region of the detected specific organ or blood vessel in a predetermined color to the switch unit 103.

In response to an operation signal transmitted from a foot switch 26, the switch unit 103 transmits the intraoperative image in frame unit received from the endoscope 19 or the organ map supplied from the region detection unit 102 to a display device 11 in FIG. 1.

(Description of Organ Map)

Figure 10:
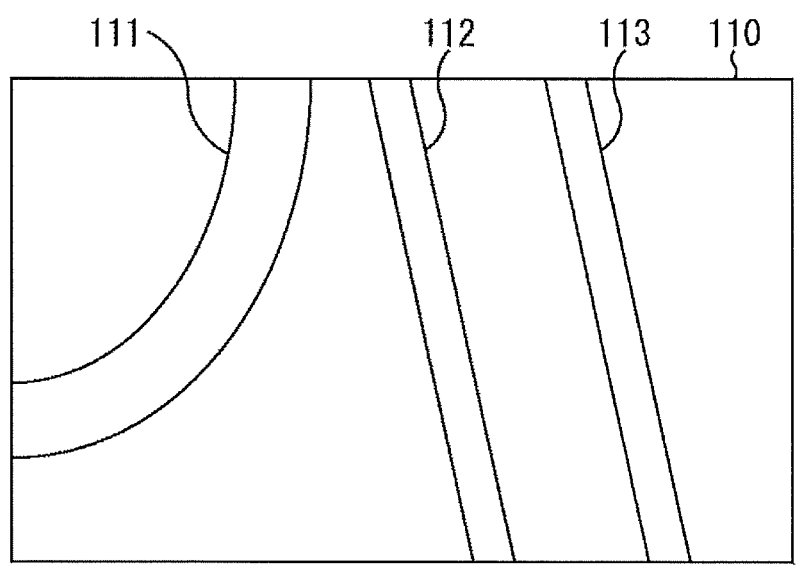
FIG. 10 is a view illustrating a detection result of a region of a blood vessel on the basis of a feature amount.
Figure 11:
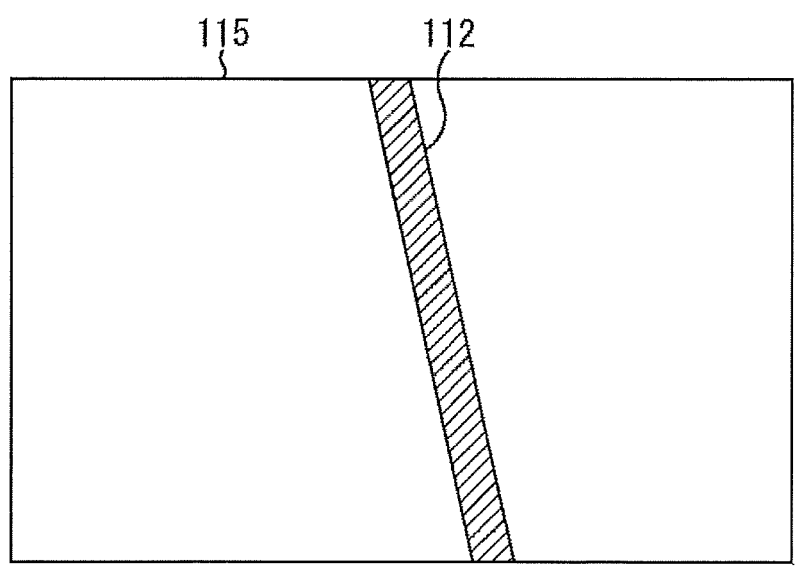
FIG. 11 is a view illustrating an organ map.

FIG. 10 is a view illustrating a detection result of the region of the blood vessel based on the feature amount, and FIG. 11 is a view illustrating the organ map.

In examples in FIGS. 10 and 11, the synchronization map generation unit 71 generates a synchronization map 80 in FIG. 7 on the basis of heartbeat information. Also, the region detection unit 102 detects the region of the blood vessel.

In this case, the region detection unit 102 first detects regions 111 to 113 of capillaries in an intraoperative image 110 as the regions of the blood vessel as illustrated in FIG. 10 on the basis of the feature amount of the intraoperative image 110. That is, the region detection unit 102 cannot discriminate the region of the blood vessel only with the feature amount of the intraoperative image 110, and detects the regions 111 to 113 of the capillaries including the blood vessel as the regions of the blood vessel.

Next, on the basis of the regions 111 to 113 and the synchronization map 80, the region detection unit 102 detects the region 112 overlapping with a region 52 included in the synchronization map 80 out of the regions 111 to 113 of the capillary as a final region of the blood vessel. That is, the region detection unit 102 discriminates the region 112 that moves synchronously with the heartbeat out of the regions 111 to 113 of the capillaries as the region of the blood vessel. Then, the region detection unit 102 generates an organ map 115 having the same size as the intraoperative image representing the region 112 in a predetermined color.

(Description of Processing of CCU)

Figure 12:
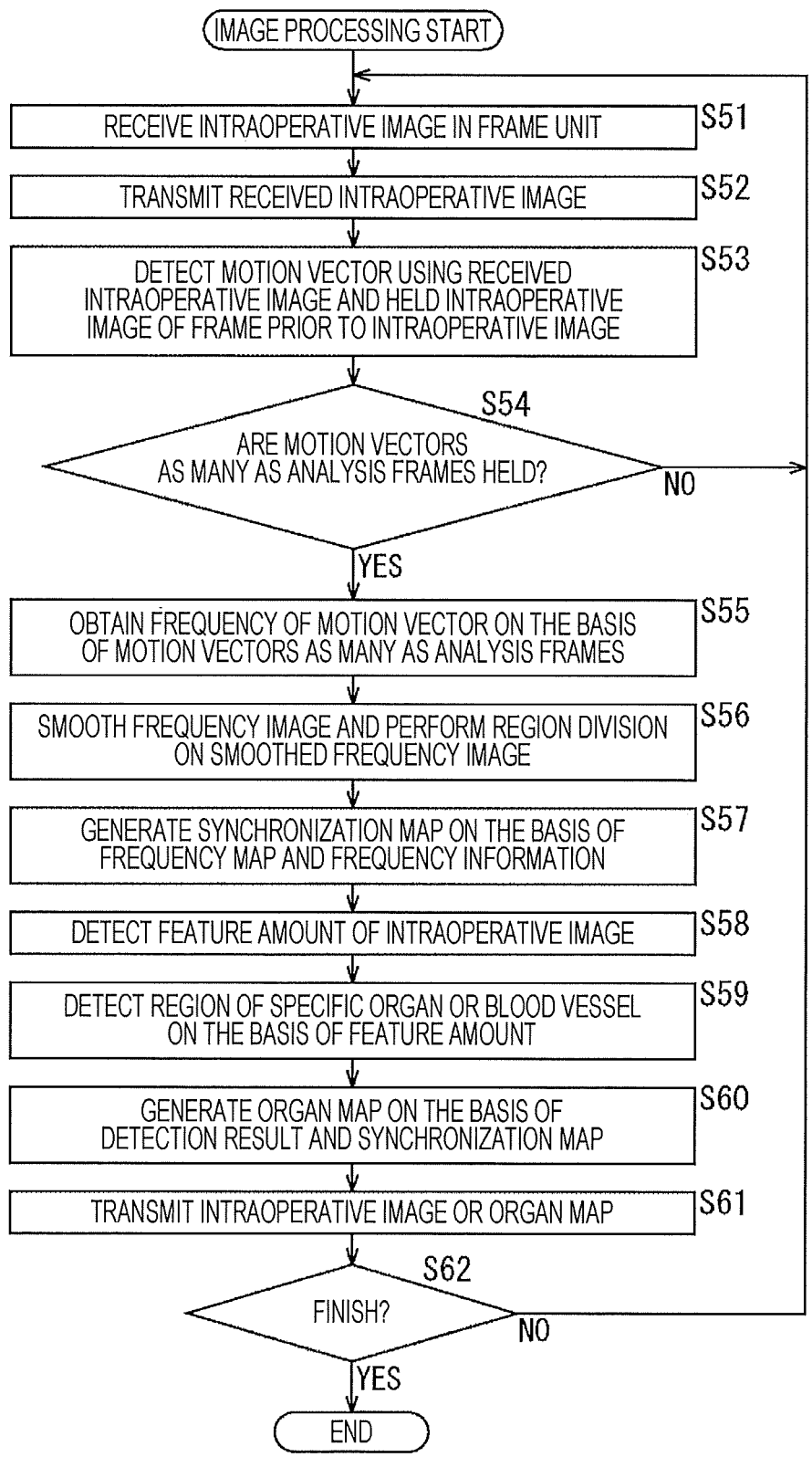
FIG. 12 is a flowchart illustrating processing of the CCU in FIG. 9.

FIG. 12 is a flowchart illustrating processing of the CCU 100 in FIG. 9.

Processes at steps S51 to S57 in FIG. 12 are same as processes at steps S31 to S37 in FIG. 8, respectively, so that description thereof is omitted.

At step S58, the feature amount detection unit 101 detects the feature amount from the intraoperative image received from the endoscope 19 and supplies the same to the region detection unit 102.

At step S59, the region detection unit 102 detects the region of the specific organ or the blood vessel on the basis of the feature amount supplied from the feature amount detection unit 101. At step S53, the region detection unit 102 generates the organ map on the basis of the detection result at step S52 and the synchronization map generated by the synchronization map generation unit 71 and supplies the same to the switch unit 103.

At step S61, the switch unit 103 transmits the intraoperative image in frame unit received by the process at immediately preceding step S51 or the organ map supplied from the region detection unit 102 to the display device 11 in response to the operation signal received from the foot switch 26.

A process at step S62 is similar to a process at step S39 in FIG. 8, so that description thereof is omitted.

In the above-described manner, since the CCU 100 detects the region of the specific organ or the blood vessel on the basis of not only the feature amount of the intraoperative image but also the synchronization map, it is possible to detect the region of the specific organ or the blood vessel with a high degree of accuracy. As a result, a surgeon and the like may discriminate the region of the specific organ or the blood vessel in the intraoperative image with a high degree of accuracy by the organ map displayed on the display device 11.

Fourth Embodiment (Configuration Example of CCU of Fourth Embodiment of Endoscopic Surgical System)

A configuration of a fourth embodiment of an endoscopic surgical system to which the present disclosure is applied is the same as that of an endoscopic surgical system 10 in FIG. 1 except for a configuration of a CCU. Therefore, only the CCU is hereinafter described.

Figure 13:
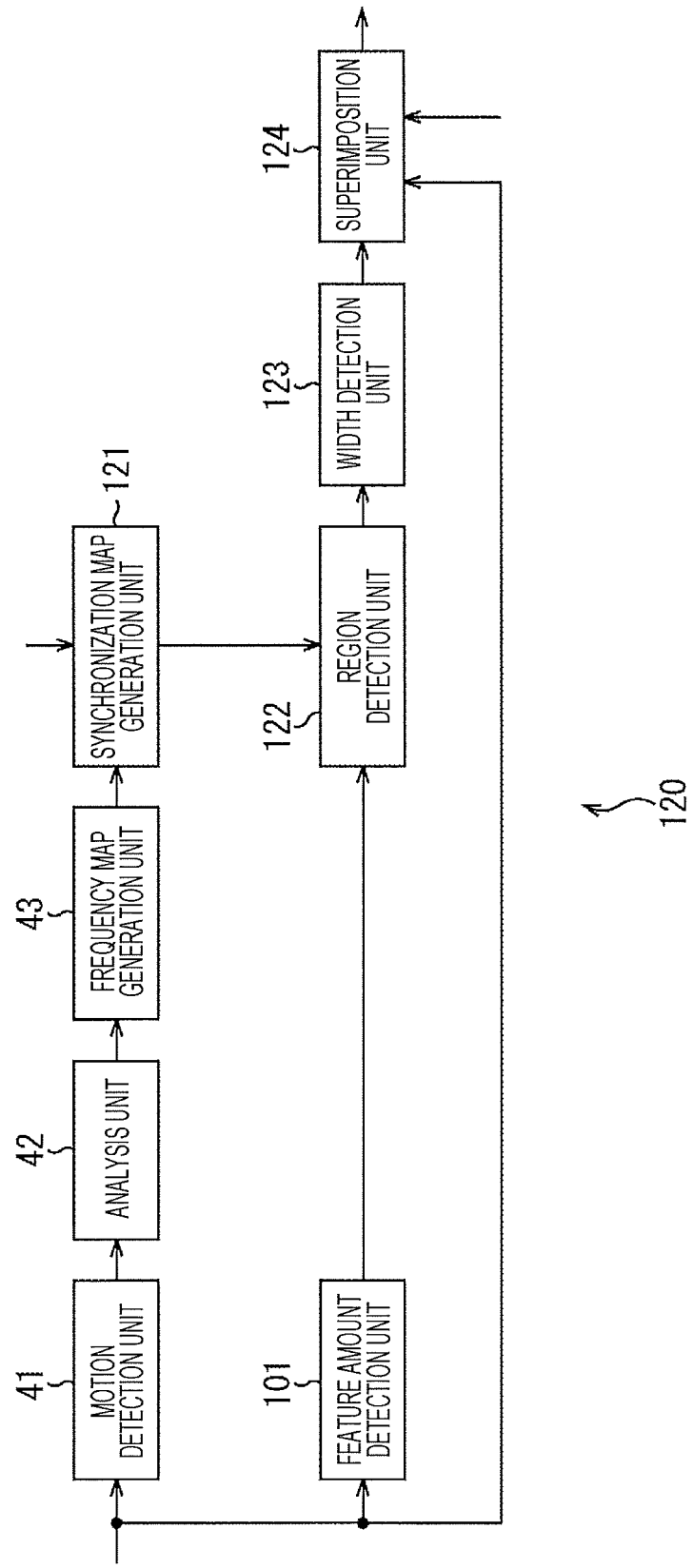
FIG. 13 is a block diagram illustrating a configuration example of a CCU according to a fourth embodiment of an endoscopic surgical system to which the present disclosure is applied.

FIG. 13 is a block diagram illustrating a configuration example of the CCU of the fourth embodiment of the endoscopic surgical system to which the present disclosure is applied.

In the configuration illustrated in FIG. 13, the same reference sign is assigned to the same configuration as that in FIG. 9. Overlapping description is appropriately omitted.

A configuration of a CCU 120 in FIG. 13 is different from a configuration of a CCU 100 in FIG. 9 in that a synchronization map generation unit 121, a region detection unit 122, and a superimposition unit 124 are provided in place of a synchronization map generation unit 71, a region detection unit 102, and a switch unit 103, respectively, and that a width detection unit 123 is newly provided. The CCU 120 detects a state of a blood vessel on the basis of width of a region of the blood vessel detected from an intraoperative image.

Specifically, the synchronization map generation unit 121 of the CCU 120 detects a region corresponding to a heartbeat out of regions in a frequency map on the basis of the frequency map supplied from a frequency map generation unit 43 and heartbeat information of the heartbeat input from an electrocardiograph not illustrated to generate a synchronization map. The synchronization map generation unit 121 supplies the synchronization map to the region detection unit 122.

The region detection unit 122 detects the region of the blood vessel on the basis of the synchronization map generated by the synchronization map generation unit 121 and a feature amount supplied from a feature amount detection unit 101. The region detection unit 122 supplies a blood vessel map having the same size as the intraoperative image representing the detected region of the blood vessel in a predetermined color to the width detection unit 123.

The width detection unit 123 (state detection unit) detects width of the region of the blood vessel in the blood vessel map supplied from the region detection unit 102 as a feature of the region of the blood vessel. The width detection unit 123 detects a hemostasis state of the blood vessel on the basis of change in time of the width of the region of the blood vessel and supplies a detection result to the superimposition unit 124.

In response to an operation signal received from a foot switch 26, the superimposition unit 124 superimposes a state notification image representing the detection result supplied from the width detection unit 123 on the intraoperative image received from an endoscope 19. For example, the state notification image is an image of a message of "hemostasis is successful" in a case where the detection result is the hemostasis state, and an image of a message of "hemostasis is unsuccessful" in a case where the detection result is not the hemostasis state.

In response to the operation signal, the superimposition unit 124 transmits the intraoperative image on which the state notification image is superimposed or the intraoperative image on which the state notification image is not superimposed to the display device 11.

(Description of Hemostasis State Detection)

Figure 14:
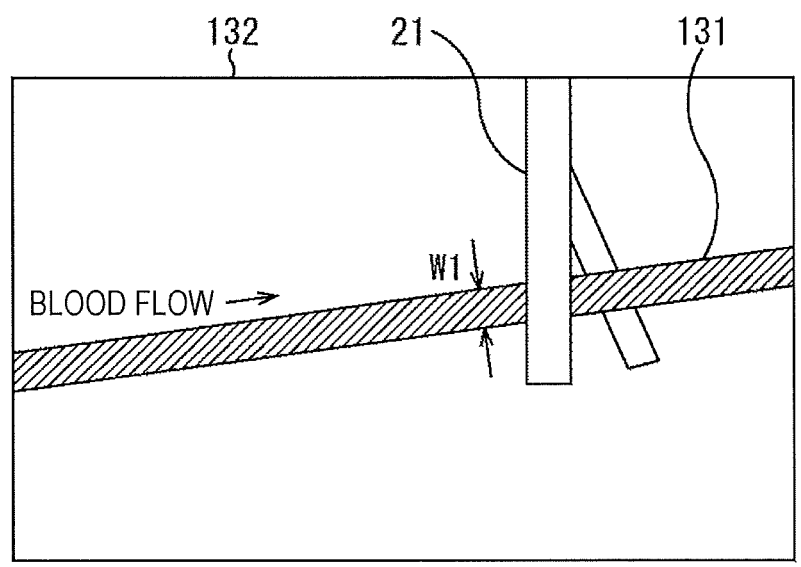
FIG. 14 is a view illustrating an example of an intraoperative image before clipping a blood vessel with forceps.
Figure 15:
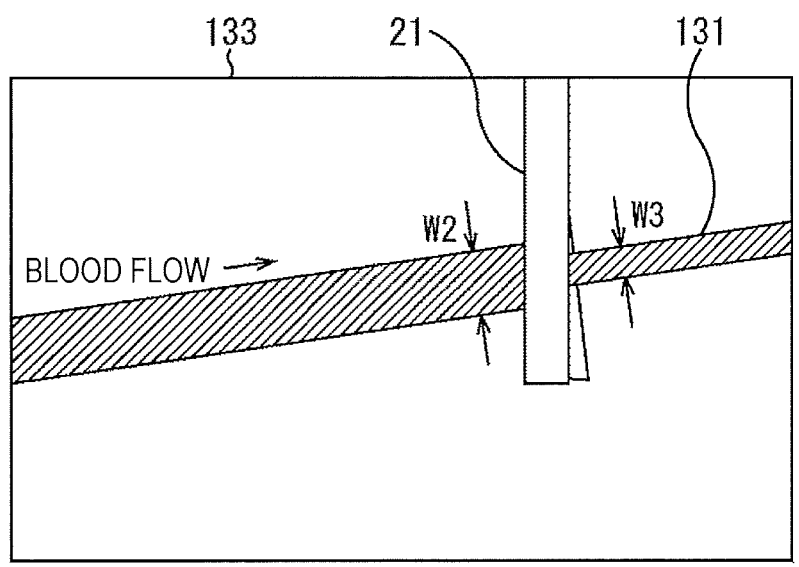
FIG. 15 is a view illustrating an example of the intraoperative image after clipping the blood vessel with the forceps.

FIG. 14 is a view illustrating an example of the intraoperative image before clipping the blood vessel with forceps 21, and FIG. 15 is a view illustrating an example of the intraoperative image after clipping the blood vessel with the forceps 21.

In a case where the region detection unit 122 detects the region of a blood vessel 131 by using an intraoperative image 132 before clipping the blood vessel 131 with the forceps 21 in FIG. 14, the width detection unit 123 detects maximum width W1 of the region of the blood vessel 131.

If a surgeon and the like clips a part of the blood vessel 131 with the forceps 21 and hemostasis is successful by this, blood pressure on an upstream side of the forceps 21 (left side in the example in FIG. 15) rises, so that as illustrated in FIG. 15, the width of the blood vessel 131 on the upstream side of the forceps 21 becomes thicker than the width W1. Also, since the blood pressure on a downstream side of the forceps 21 (right side in the example in FIG. 15) is lowered, the width of the blood vessel 131 on the downstream side of the forceps 21 becomes thinner than the width W1.

That is, maximum width W2 of the region of the blood vessel 131 extracted by using an intraoperative image 133 after the blood vessel 131 is clipped with the forceps 21 in FIG. 15 by the region detection unit 122 is thicker than the width W1, and minimum width W3 is thinner than the width W1. Therefore, in a case where the maximum width of the blood vessel 131 becomes thicker, the width detection unit 123 detects that the state of the blood vessel 131 is the hemostasis state.

On the other hand, in a case where the hemostasis is unsuccessful, no change in blood pressure due to the forceps 21 occurs, and the maximum width of the region of the blood vessel 131 is the same as the width W1. Accordingly, in a case where the maximum width of the blood vessel 131 does not change, the width detection unit 123 detects that the state of the blood vessel 131 is not the hemostasis state.

Meanwhile, in a case where the blood vessel 131 is clipped with the forceps 21 in a state where the blood vessel 131 is damaged and it bleeds therefrom, clipping is performed at an end of the region of the blood vessel 131, so that there is no blood vessel 131 on the downstream side of the forceps 21. However, even in this case, since the blood pressure on the upstream side of the forceps 21 rises, the width of the blood vessel 131 on the upstream side of the forceps 21 becomes thicker than the width W1, so that it is possible to detect the hemostasis state of the blood vessel by whether the maximum width of the blood vessel 131 becomes thicker than W1.

(Description of Processing of CCU)

Figure 16:
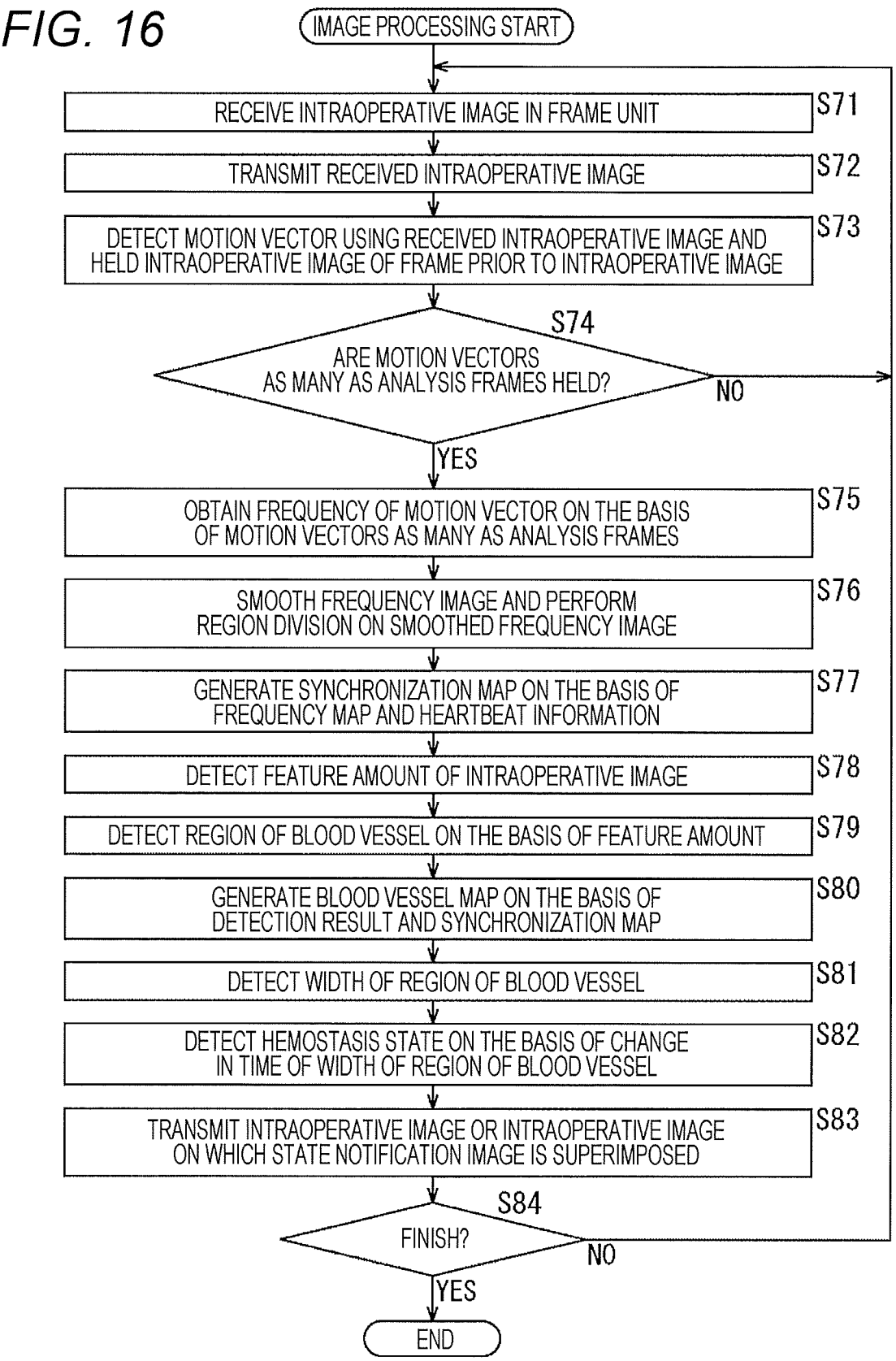
FIG. 16 is a flowchart illustrating processing of the CCU in FIG. 13.

FIG. 16 is a flowchart illustrating processing of the CCU 120 in FIG. 13.

Processes at steps S71 to S76 in FIG. 16 are similar to processes at steps S51 to S56 in FIG. 12, respectively, so that description thereof is omitted.

At step S77, the synchronization map generation unit 121 of the CCU 120 generates the synchronization map on the basis of the frequency map supplied from the frequency map generation unit 43 and the heartbeat information of the heartbeat input from the electrocardiograph not illustrated and the like. The synchronization map generation unit 121 supplies the synchronization map to the region detection unit 122.

At step S78, the feature amount detection unit 101 detects the feature amount from the intraoperative image received from the endoscope 19 and supplies the same to the region detection unit 122.

At step S79, the region detection unit 122 detects the region of the blood vessel on the basis of the feature amount supplied from the feature amount detection unit 101. At step S80, the region detection unit 122 generates the blood vessel map on the basis of the detection result at step S79 and the synchronization map supplied from the synchronization map generation unit 121 and supplies the same to the width detection unit 123.

At step S81, the width detection unit 123 detects the width of the region of the blood vessel in the blood vessel map supplied from the region detection unit 102.

At step S82, the width detection unit 123 detects the hemostasis state of the blood vessel on the basis of the change in time of the width of the region of the blood vessel, and supplies the detection result to the superimposition unit 124. In response the operation signal received from the foot switch 26, the superimposition unit 124 superimposes the state notification image representing the detection result supplied from the width detection unit 123 on the intraoperative image received by the process at immediately preceding step S72.

At step S83, the superimposition unit 124 transmits the intraoperative image received from the endoscope 19 by the process at immediately preceding step S72 or the intraoperative image on which the state notification image is superimposed to the display device 11.

A process at step S84 is similar to a process at step S62 in FIG. 12, so that description thereof is omitted.

Fifth Embodiment (Configuration Example of CCU of Fifth Embodiment of Endoscopic Surgical System)

A configuration of a fifth embodiment of an endoscopic surgical system to which the present disclosure is applied is the same as a configuration of an endoscopic surgical system 10 in FIG. 1 except for a configuration of a CCU. Therefore, only the CCU is hereinafter described.

Figure 17:
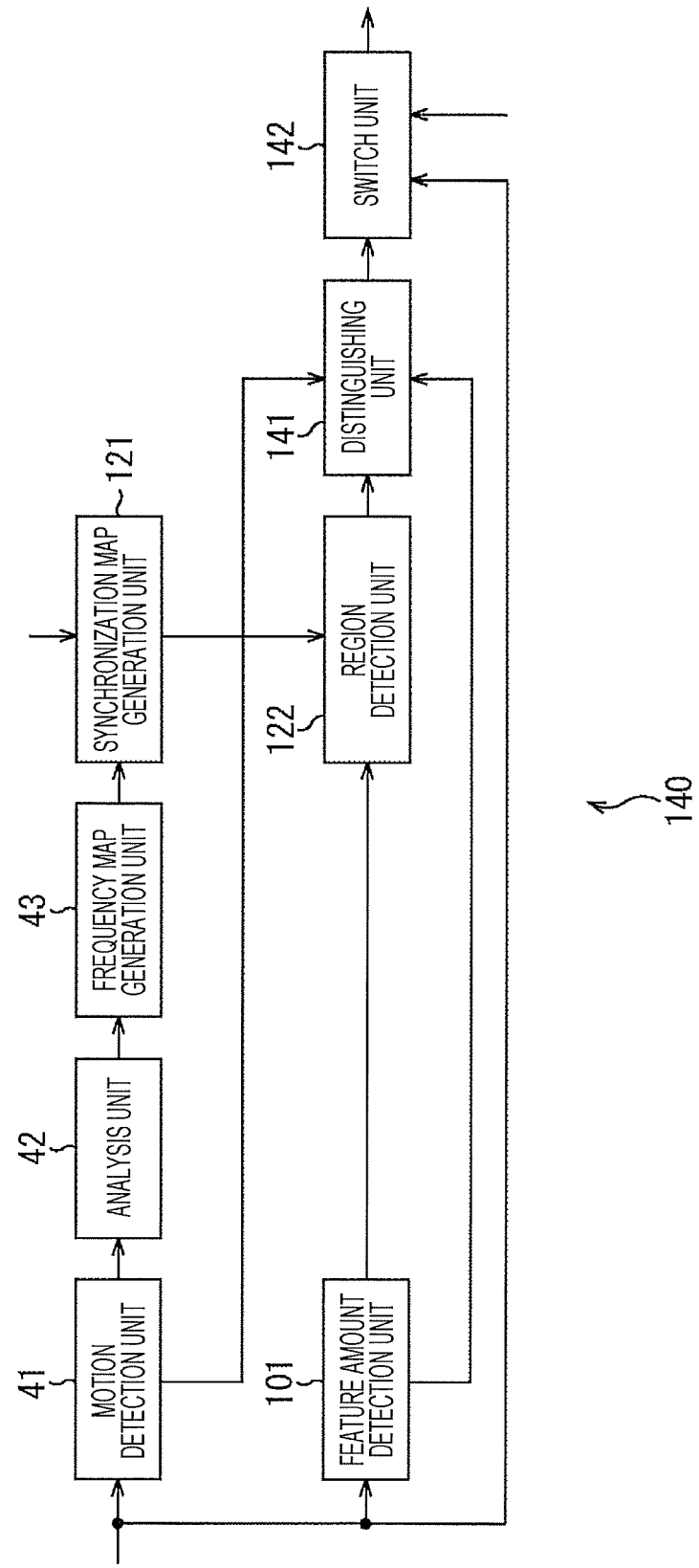
FIG. 17 is a block diagram illustrating a configuration example of a CCU according to a fifth embodiment of an endoscopic surgical system to which the present disclosure is applied.

FIG. 17 is a block diagram illustrating a configuration example of the CCU according to the fifth embodiment of the endoscopic surgical system to which the present disclosure is applied.

In the configuration illustrated in FIG. 17, the same reference sign is assigned to the same configuration as that in FIG. 13. Overlapping description is appropriately omitted.

A configuration of a CCU 140 in FIG. 17 is different from a configuration of a CCU 120 in FIG. 13 in that a distinguishing unit 141 and a switch unit 142 are provided in place of a width detection unit 123 and a superimposition unit 124, respectively. The CCU 140 distinguishes between a region of an artery and a region of a vein out of regions of blood vessels on the basis of a motion vector and a feature amount of an intraoperative image.

Specifically, on the basis of the motion vector detected by a motion detection unit 41 and the feature amount of the intraoperative image detected by a feature amount detection unit 101, the distinguishing unit 141 of the CCU 140 distinguishes whether the region of the blood vessel in a blood vessel map generated by a region detection unit 122 is the region of the artery or the region of the vein.

That is, in general, arterial blood has higher luminance and saturation than venous blood, and its hue is on a positive side (spectral characteristic is on a longer wavelength side). Also, since adjacent blood vessels are often a pair of the artery and vein, directions of blood flows are often opposed to each other. Furthermore, the artery is more pulsatile than the vein.

From above, the distinguishing unit 141 performs principal component analysis and the like on the basis of the motion vector and color information out of the feature amount of the region of the blood vessel in the blood vessel map, thereby distinguishing whether the region is the region of the artery or the region of the vein. That is, the distinguishing unit 141 distinguishes a type of the blood vessel included in the region of the blood vessel. The distinguishing unit 141 generates an arteriovenous map by making colors of the region of the vein and the region of the artery in the blood vessel map different on the basis of a distinguishing result of each region and supplies the same to the switch unit 142.

In response to an operation signal received from a foot switch 26, the switch unit 142 transmits the intraoperative image received from an endoscope 19 or the arteriovenous map supplied from the distinguishing unit 141 to a display device 11.

(Example of Arteriovenous Map)

Figure 18:
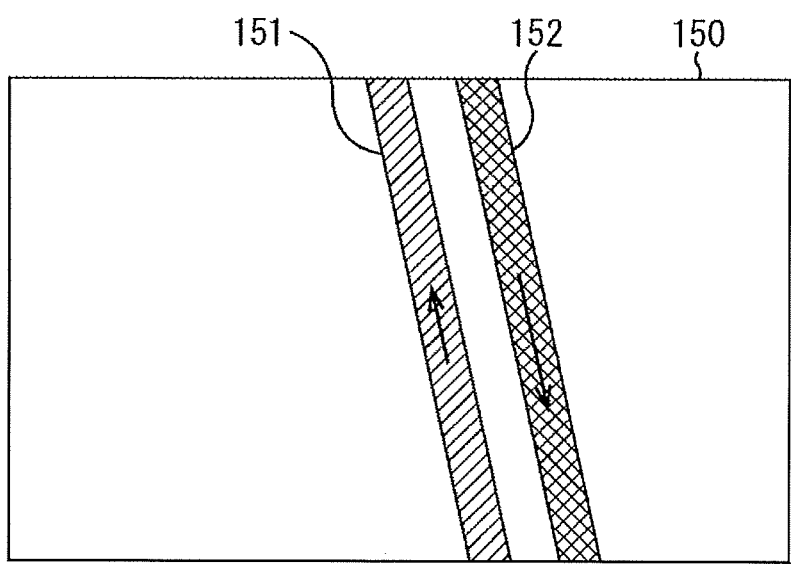
FIG. 18 is a view illustrating an example of an arteriovenous map.

FIG. 18 is a view illustrating an example of the arteriovenous map.

For example, the distinguishing unit 141 distinguishes one of the pair of the regions of the blood vessels adjacent to each other with positive and negative opposite average values of the motion vector values in a horizontal direction or a vertical direction, the one with large motion amount, luminance, and saturation and with the hue on the positive side as the region of the artery and distinguishes the other as the region of the vein.

As a result, as illustrated in FIG. 18, colors of regions 151 and 152 of the adjacent blood vessels in the arteriovenous map 150 are different from each other. For example, the color of the region 151 in the arteriovenous map 150 is the color representing the region of the vein, and the color of the region 152 is the color representing the region of the artery.

(Description of Processing of CCU)

Figure 19:
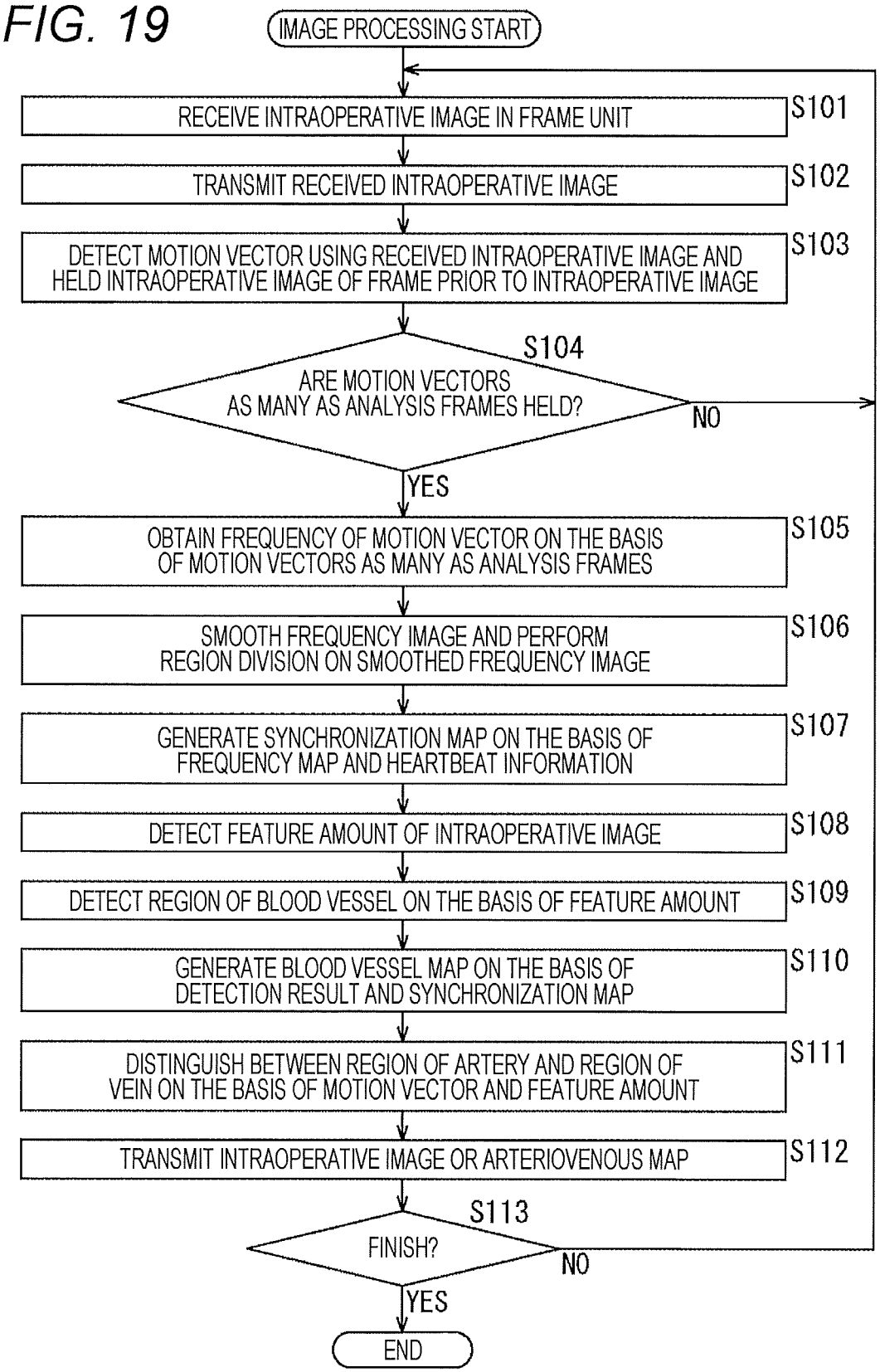
FIG. 19 is a flowchart illustrating image processing of the CCU in FIG. 17.

FIG. 19 is a flowchart illustrating image processing of the CCU 140 in FIG. 17.

Processes at steps S101 to S110 in FIG. 19 are similar to processes at steps S71 to S80 in FIG. 16, respectively, so that description thereof is omitted.

At step S111, on the basis of the motion vector and the feature amount of the intraoperative image, the distinguishing unit 141 of the CCU 140 distinguishes whether the region of the blood vessel in the blood vessel map is the region of the artery or the region of the vein, and generates the arteriovenous map. The distinguishing unit 141 supplies the arteriovenous map to the switch unit 142.

At step S112, the switch unit 142 transmits the intraoperative image received from the endoscope 19 or the arteriovenous map supplied from the distinguishing unit 141 to the display device 11 in response to the operation signal received from the foot switch 26.

A process at step S113 is similar to a process at step S84 in FIG. 16, so that description thereof is omitted.

As described above, the CCU 140 distinguishes between the region of the artery and the region of the vein out of the regions of the blood vessels on the basis of the feature amount of the intraoperative image and the motion vector. Therefore, it is possible to distinguish between the region of the artery and the region of the vein with a high degree of accuracy.

On the other hand, in a case of distinguishing between the region of the artery and the region of the vein using only the color information, the color information changes depending on an illumination state at the time of capturing the intraoperative image and depth of the blood vessel, so that it is difficult to distinguish between the region of the artery and the region of the vein with a high degree of accuracy.

Meanwhile, although it is distinguished between the region of the artery and the region of the vein on the basis of both the feature amount of the intraoperative image and the motion vector in the fifth embodiment, it is also possible to distinguish on the basis of either one of them.

Sixth Embodiment (Configuration Example of CCU of Sixth Embodiment of Endoscopic Surgical System)

A configuration of a sixth embodiment of an endoscopic surgical system to which the present disclosure is applied is the same as that of an endoscopic surgical system 10 in FIG. 1 except for a configuration of a CCU. Therefore, only the CCU is hereinafter described.

Figure 20:
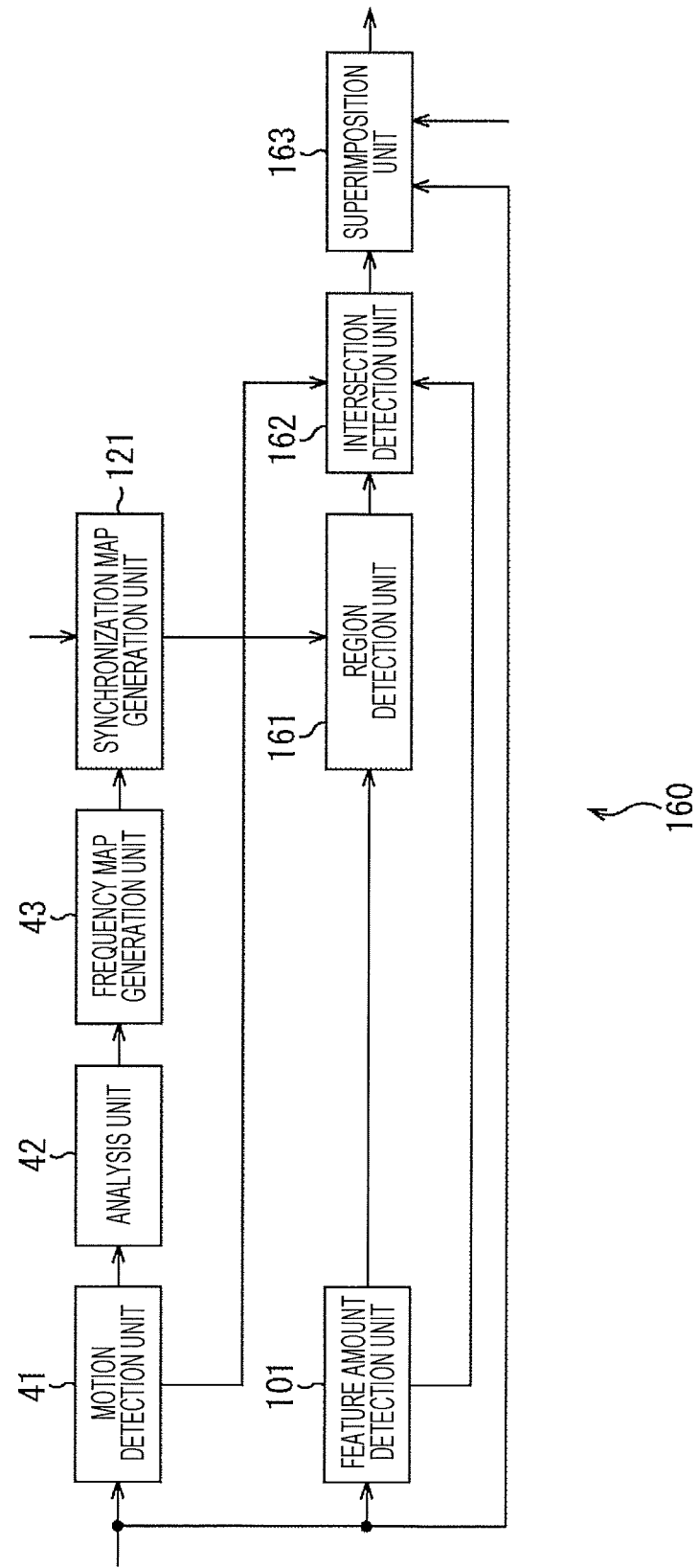
FIG. 20 is a block diagram illustrating a configuration example of a CCU according to a sixth embodiment of an endoscopic surgical system to which the present disclosure is applied.

FIG. 20 is a block diagram illustrating a configuration example of the CCU according to the sixth embodiment of the endoscopic surgical system to which the present disclosure is applied.

In the configuration illustrated in FIG. 20, the same reference sign is assigned to the same configuration as that in FIG. 17. Overlapping description is appropriately omitted.

A configuration of a CCU 160 in FIG. 20 differs from a configuration of a CCU 140 in FIG. 17 in that a region detection unit 161, an intersection detection unit 162, and a superimposition unit 163 are provided in place of a region detection unit 122, a distinguishing unit 141, and a switch unit 142, respectively. The CCU 160 detects a bleeding region on the basis of a synchronization map and a feature amount and detects a bleeding point on the basis of a motion vector of the bleeding region.

Specifically, the region detection unit 161 of the CCU 160 detects the bleeding region on the basis of the synchronization map generated by a synchronization map generation unit 121 and the feature amount supplied from a feature amount detection unit 101.

That is, since blood flows out in synchronization with a heartbeat, the region detection unit 161 detects, for example, a region having a size equal to or larger than a predetermined size having red color information as the feature amount, the region synchronizing with a heartbeat in the synchronization map as the bleeding region. The region detection unit 122 supplies a bleeding map having the same size as an intraoperative image representing the detected bleeding region in a predetermined color to the intersection detection unit 162.

The intersection detection unit 162 detects an intersection of lines obtained by extending starting points of the motion vectors of bleeding in the bleeding region of the bleeding map supplied from the region detection unit 161 out of the motion vectors supplied from the motion detection unit 41 as the bleeding point. The intersection detection unit 162 supplies bleeding point information indicating a position in the intraoperative image of the bleeding point to the superimposition unit 163.

In response to an operation signal received from a foot switch 26, the superimposition unit 163 superimposes a bleeding point image representing the bleeding point on the position of the bleeding point indicated by the bleeding point information supplied from the intersection detection unit 162 in the intraoperative image received from an endoscope 19. The intersection detection unit 162 transmits the intraoperative image received from the endoscope 19 or the intraoperative image on which the bleeding point image is superimposed to a display device 11 in FIG. 1.

(Description of Detection of Bleeding Point)

Figure 21:
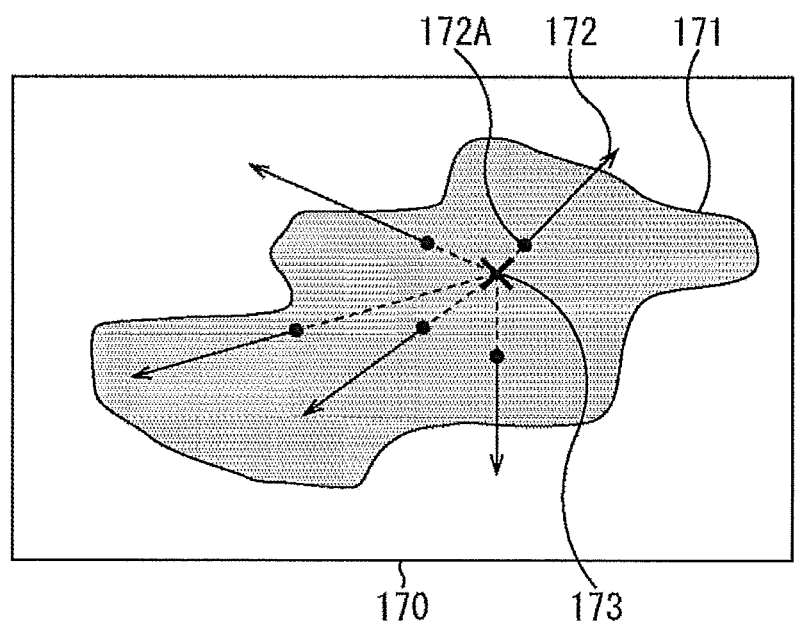
FIG. 21 is a view illustrating detection of a bleeding point.

FIG. 21 is a view illustrating the detection of the bleeding point by the intersection detection unit 162 in FIG. 20.

When bleeding occurs, the blood flows radially from the bleeding point. Therefore, it is estimated that motion vectors 172 in a bleeding region 171 in a bleeding map 170 are radially distributed from the bleeding point. Therefore, as illustrated in FIG. 21, the intersection detection unit 162 extends a starting point 172A of each motion vector 172 in a direction opposite to a direction of the motion vector 172 and detects an intersection point 173 of the extended motion vectors 172 as the bleeding point.

(Description of Processing of CCU)

Figure 22:
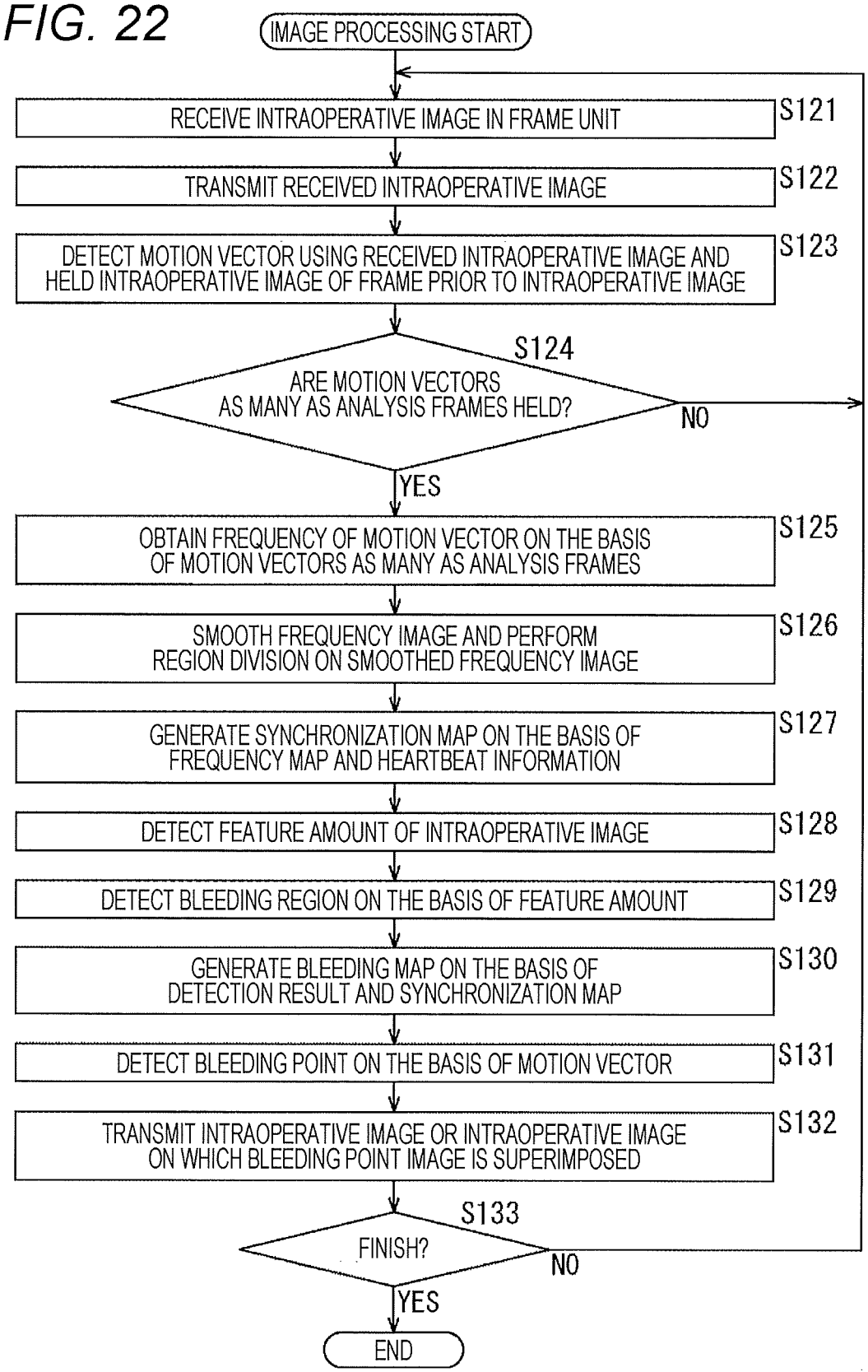
FIG. 22 is a flowchart illustrating image processing in FIG. 20.
Figure 23:
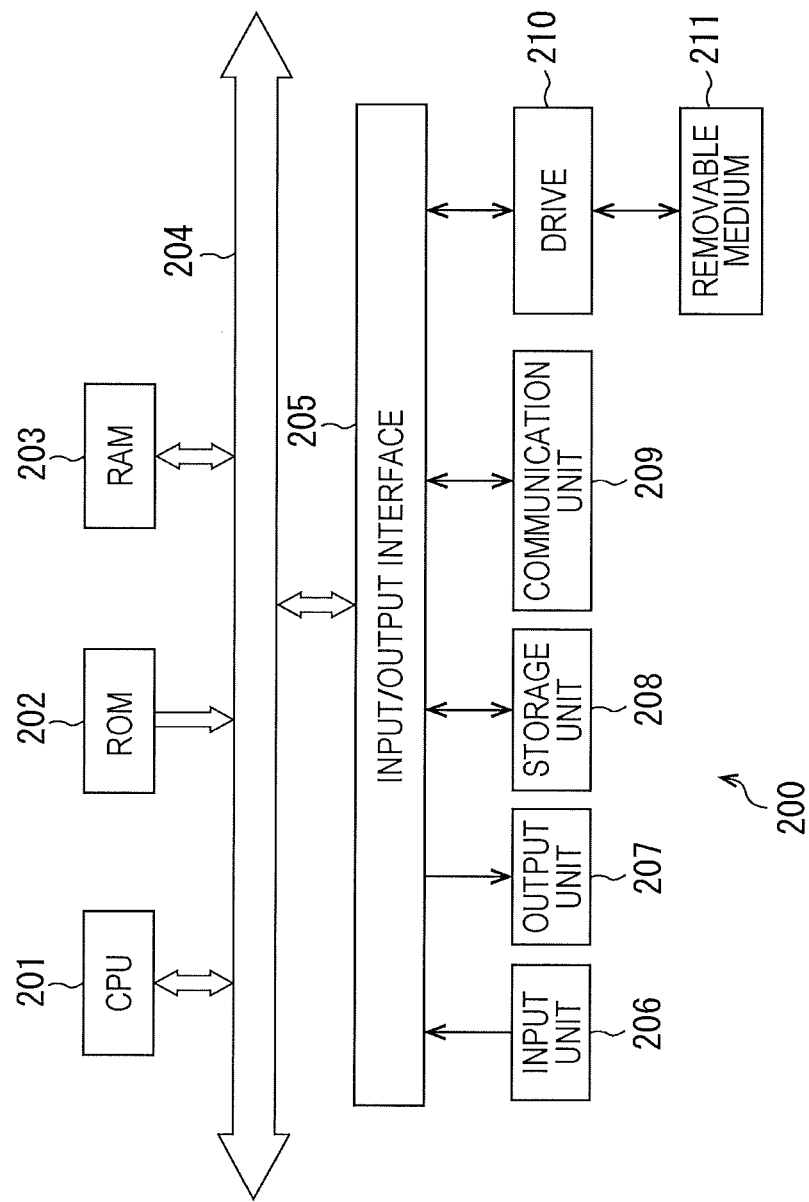
FIG. 23 is a block diagram illustrating a configuration example of hardware of a computer.

FIG. 22 is a flowchart illustrating image processing of the CCU 160 in FIG. 20.

Processes at steps S121 to S128 in FIG. 22 are similar to processes at steps S101 to S118 in FIG. 19, respectively, so that description thereof is omitted.

At step S129, the region detection unit 161 of the CCU 160 detects a red region having a size equal to or larger than a predetermined size as the bleeding region on the basis of the color information out of the feature amounts supplied from the feature amount detection unit 101.

At step S130, the region detection unit 161 generates the bleeding map on the basis of a detection result by the process at step S129 and the synchronization map generated by the synchronization map generation unit 121. Specifically, the region detection unit 161 detects the bleeding region detected by the process at step S129 out of the region in the synchronization map as a final bleeding region. Then, the region detection unit 161 generates the bleeding map on the basis of the detected bleeding region and supplies the same to the intersection detection unit 162.

At step S131, the intersection detection unit 162 detects the intersection of the lines obtained by extending the staring points of the motion vectors in the bleeding region in the bleeding map supplied from the region detection unit 161 out of the motion vectors supplied from the motion detection unit 41 as the bleeding point. The intersection detection unit 162 supplies the bleeding point information to the superimposition unit 163.

In response to the operation signal received from the foot switch 26, the superimposition unit 163 superimposes the bleeding point image on the position of the bleeding point indicated by the bleeding point information supplied from the intersection detection unit 162 in the intraoperative image received from the endoscope 19.

At step S132, the intersection detection unit 162 transmits the intraoperative image received from the endoscope 19 or the intraoperative image on which the bleeding point image is superimposed to the display device 11 in FIG. 1 in response to the operation signal received from the foot switch 26.

A process at step S133 is similar to a process at step S113 in FIG. 19, so that description thereof is omitted.

As described above, the CCU 160 detects the bleeding point on the basis of the motion vectors of the intraoperative image. Therefore, the CCU 160 may superimpose the bleeding point image on the intraoperative image to display on the display device 11. As a result, a surgeon and the like may easily recognize the position of the bleeding point.

On the other hand, in a case where the bleeding point image is not displayed on the display device 11, if a bleeding amount is large, the periphery of the bleeding point in the intraoperative image becomes entirely red and it is difficult to recognize the bleeding point.

Seventh Embodiment (Description of Computer to which this Technology is Applied)

A series of processes described above may be executed by hardware or by software. In a case where a series of processes is performed by the software, a program which forms the software is installed on a computer. Herein, the computer includes a computer built in dedicated hardware, a general-purpose personal computer, for example, capable of executing various functions by various programs installed and the like.

FIG. 23 is a block diagram illustrating a configuration example of hardware of a computer which executes a series of processes described above by a program.

In a computer 200, a central processing unit (CPU) 201, a read only memory (ROM) 202, and a random-access memory (RAM) 203 are connected to one another through a bus 204.

An input/output interface 205 is further connected to the bus 204. An input unit 206, an output unit 207, a storage unit 208, a communication unit 209, and a drive 210 are connected to the input/output interface 205.

The input unit 206 is formed or a keyboard, a mouse, a microphone and the like. The output unit 207 is formed of a display, a speaker and the like. The storage unit 208 is formed of a hard disk, a non-volatile memory and the like. The communication unit 209 is formed of a network interface and the like. The drive 210 drives a removable medium 211 such as a magnetic disk, an optical disk, a magnetooptical disk, or a semiconductor memory.

In the computer 200 configured in the above-described manner, the CPU 201 loads the program stored in the storage unit 208, for example, on the RAM 203 through the input/output interface 205 and the bus 204 to execute, so that a series of processes described above is performed. A midstream result of the process and information used for the process are stored in the ROM 202, the RAM 203 and the like.

The program executed by the computer 200 (CPU 201) may be recorded on the removable medium 211 as a package medium and the like to be provided, for example. Also, the program may be provided by means of a wired or wireless transmission medium such as a local region network, the Internet, and digital broadcasting.

In the computer 200, the program may be installed on the storage unit 208 through the input/output interface 205 by mounting the removable medium 211 on the drive 210. Also, the program may be received by the communication unit 209 through the wired or wireless transmission medium to be installed on the storage unit 208. In addition, the program may be installed in advance on the ROM 202 and the storage unit 208.

Meanwhile, the program executed by the computer 200 may be the program of which processes are performed in time series in the order described in this specification or may be the program of which processes are performed in parallel or at required timing such as when a call is issued.

In this specification, a system is intended to mean assembly of a plurality of components (devices, modules (parts) and the like) and it does not matter whether all the components are in the same casing. Therefore, a plurality of devices accommodated in different casings connected through the network and one device obtained by accommodating a plurality of modules in one casing are the systems.

Meanwhile, the effect described in this specification is illustrative only; the effect is not limited thereto and there may also be another effect.

Also, the embodiment of the present disclosure is not limited to the above-described embodiments and various modifications may be made without departing from the gist of the present disclosure.

For example, the frequency map, the synchronization map, the organ map, and the arteriovenous map may be superimposed on the intraoperative image to be displayed or may be displayed in parallel on the same screen as the intraoperative image.

Also, the detection of the region of the blood vessel in the fourth and fifth embodiments and the detection of the bleeding region in the sixth embodiment may also be performed on the basis of only the feature amount of the intraoperative image, of this may also be performed on the basis of only the synchronization map.

Furthermore, in the fourth embodiment, it is also possible to distinguish between the hemostatic state of the arterial vessel and that of the venous vessel distinguished in the fifth embodiment. Also, at least two of the first to sixth embodiments may be combined so that at least two of the frequency map, the synchronization map, the organ map, the state notification map, the arteriovenous map, and the bleeding point image may be generated.

Also, the present technology may also be applied to a surgical system other than the endoscopic surgical system as long as this is a surgical system that captures an intraoperative image and performs image processing. For example, the present technology may also be applied to a surgical system and the like that captures the intraoperative image with a video microscope and performs image processing.

Meanwhile, the present disclosure may also have the following configurations.

(1)

An image processing device including:

a motion detection unit that detects a motion vector of a living body in an intraoperative image using intraoperative images at different times;

an analysis unit that obtains a frequency of the motion vector detected by the motion detection unit; and a region detection unit that detects a region including a specific living body site in the intraoperative image on the basis of the frequency obtained by the analysis unit.

(2)

The image processing device according to (1) described above, in which the region detection unit is configured to detect, for each frequency, the region including the specific living body site corresponding to the frequency.

(3)

The image processing device according to (1) described above, in which the region detection unit is configured to detect the region including the specific living body site corresponding to a predetermined frequency.

(4)

The image processing device according to (3) described above, in which the predetermined frequency is configured to be determined on the basis of heartbeat information.

(5)

The image processing device according to (1) described above, in which the region detection unit is configured to detect the region on the basis of the frequency and a feature amount of the intraoperative image.

(6)

The image processing device according to (5) described above, in which the region is configured to include a specific organ or a blood vessel.

(7)

The image processing device according to any one of (1) to (6) described above, further including:

a state detection unit that detects a state of the region on the basis of a feature of the region detected by the region detection unit.

(8)

The image processing device according to (7) described above, in which the region is a region including a blood vessel, and the state detection unit is configured to detect a hemostasis state of the blood vessel on the basis of width of the blood vessel.

(9)

The image processing device according to (7) or (8) described above, further including:

a superimposition unit that superimposes a state notification image generated on the basis of the state of the region on the intraoperative image.

(10)

The image processing device according to any one of (1) to (9) described above, further including:

a distinguishing unit that distinguishes a type of the specific living body site included in the region detected by the region detection unit on the basis of the motion vector detected by the motion detection unit.

(11)

The image processing device according to (10) described above, in which the distinguishing unit is configured to distinguish the type of the specific living body site on the basis of the motion vector detected by the motion detection unit and a feature amount of the intraoperative image.

(12)

The image processing device according to (10) or (11) described above, in which the region is a region including a blood vessel, and the distinguishing unit is configured to distinguish whether the blood vessel is an artery or a vein.

(13)

The image processing device according to any one of (1) to (12) described above, further including:

an intersection detection unit that detects an intersection of motion vectors of the specific living body site in the region detected by the region detection unit.

(14)

The image processing device according to (13) described above, in which the region detection unit is configured to detect a region including bleeding on the basis of the frequency and a feature amount of the intraoperative image, and the intersection detection unit is configured to detect a bleeding point on the basis of the intersection of the motion vectors of the bleeding in the region.

(15)

An image processing method including:

a motion detecting step of detecting a motion vector of a living body in an intraoperative image using intraoperative images at different times;

an analyzing step of obtaining a frequency of the motion vector detected by a process at the motion detecting step; and a region detecting step of detecting a region including a specific living body site in the intraoperative image on the basis of the frequency obtained by a process at the analyzing step by an image processing device.

(16)

A surgical system including:

an imaging device that captures an intraoperative image; and an image processing device that performs image processing on the intraoperative image, in which the image processing device is provided with:

a motion detection unit that detects a motion vector of a living body in the intraoperative image using intraoperative images at different times, an analysis unit that obtains a frequency of the motion vector detected by the motion detection unit, and a region detection unit that detects a region including a specific living body site in the intraoperative image on the basis of the frequency obtained by the analysis unit.

(17)

The surgical system according to (16) described above, in which the imaging device that captures the intraoperative image is configured to be an endoscope.

(18)

The surgical system according to (16) described above, in which the imaging device that captures the intraoperative image is configured to be a video microscope.

REFERENCE SIGNS LIST

12 CCU
19 Endoscope
41 Motion detection unit
42 Analysis unit
43 Frequency map generation unit
70 CCU
71 Synchronization map generation unit
100 CCU
102 Region detection unit
120 CCU
122 Region detection unit
123 Width detection unit
140 CCU
141 Distinguishing unit
160 CCU
161 Region detection unit
162 Intersection detection unit

The invention claimed is:

1. An image processing device comprising:
a motion detector that detects a motion vector of a living body in an intraoperative image using intraoperative images at different times;

an analyzer that obtains a frequency of the motion vector detected by the motion detector;

a region detector that detects a region including a specific living body site in the intraoperative image on the basis of the frequency obtained by the analyzer; and an intersection detector that detects an intersection of motion vectors of the specific living body site in the region detected by the region detector.

2. The image processing device according to claim 1, wherein the region detector is to detect, for each frequency, the region including the specific living body site corresponding to the frequency.

3. The image processing device according to claim 1, wherein the region detector is to detect the region including the specific living body site corresponding to a predetermined frequency.

4. The image processing device according to claim 3, wherein the predetermined frequency is to be determined on the basis of heartbeat information.

5. The image processing device according to claim 1, wherein the region detector is to detect the region on the basis of the frequency and a feature amount of the intraoperative image.

6. The image processing device according to claim 5, wherein the region includes a specific organ or a blood vessel.

7. The image processing device according to claim 1, further comprising:

a state detector that detects a state of the region on the basis of a feature of the region detected by the region detector.

8. The image processing device according to claim 7, wherein the region is a region including a blood vessel, and the state detector detects a hemostasis state of the blood vessel on the basis of width of the blood vessel.

9. The image processing device according to claim 7, further comprising:

a superimposer that superimposes a state notification image generated on the basis of the state of the region on the intraoperative image.

10. The image processing device according to claim 1, further comprising:

a distinguisher that distinguishes a type of the specific living body site included in the region detected by the region detector on the basis of the motion vector detected by the motion detector.

11. The image processing device according to claim 10, wherein the distinguisher is to distinguish the type of the specific living body site on the basis of the motion vector detected by the motion detector and a feature amount of the intraoperative image.

12. The image processing device according to claim 10, wherein the region is a region including a blood vessel, and the distinguisher is to distinguish whether the blood vessel is an artery or a vein.

13. The image processing device according to claim 1, wherein the region detector to detect a region including bleeding on the basis of the frequency and a feature amount of the intraoperative image, and the intersection detector to detect a bleeding point on the basis of the intersection of the motion vectors of the bleeding in the region.

14. An image processing method comprising:

detecting a motion vector of a living body in an intraoperative image using intraoperative images at different times;

obtaining a frequency of the motion vector;

detecting a region including a specific living body site in the intraoperative image on the basis of the frequency obtained; and detecting an intersection of motion vectors of the specific living body site in the region detected.

15. A surgical system comprising:

an imaging device that captures an intraoperative image; and an image processing device that performs image processing on the intraoperative image, wherein the image processing device is provided with:

a motion detector that detects a motion vector of a living body in the intraoperative image using intraoperative images at different times, an analyzer that obtains a frequency of the motion vector detected by the motion detector, a region detector that detects a region including a specific living body site in the intraoperative image on the basis of the frequency obtained by the analyzer, and an intersection detector that detects an intersection of motion vectors of the specific living body site in the region detected by the region detector.

16. The surgical system according to claim 15, wherein the imaging device that captures the intraoperative image is an endoscope.

17. The surgical system according to claim 15, wherein the imaging device that captures the intraoperative image is a video microscope.

* * * * *